(12) United States Patent
Buzatu et al.

(10) Patent No.: US 7,824,660 B2
(45) Date of Patent: Nov. 2, 2010

(54) NANOTUBES FOR CANCER THERAPY AND DIAGNOSTICS

(76) Inventors: Dan A. Buzatu, 1907 Durwood St., Benton, AR (US) 72015; Jon G. Wilkes, 5001 Lee Ave., Little Rock, AR (US) 72205; Dwight Miller, 2901 Dan Rd., White Hall, AR (US) 72029; Jerry A. Darsey, 2801 S. University Ave., University of Arkansas, Little Rock, AR (US) 72204; Tom Heinze, 201 Wesley La., White Hall, AR (US) 71602; Alex Birls, 11718 Shady Ridge Dr., Little Rock, AR (US) 72211; Richard Beger, 101 Blue Bird Cove, White Hall, AR (US) 71602

( * ) Notice: Subject to any disclaimer, the term of this patent is extended or adjusted under 35 U.S.C. 154(b) by 129 days.

(21) Appl. No.: 12/112,986

(22) Filed: Apr. 30, 2008

(65) Prior Publication Data

US 2009/0022655 A1  Jan. 22, 2009

Related U.S. Application Data

(63) Continuation-in-part of application No. 11/005,412, filed on Dec. 6, 2004, now abandoned.

(60) Provisional application No. 60/527,454, filed on Dec. 5, 2003, provisional application No. 60/553,907, filed on Mar. 17, 2004.

(51) Int. Cl.
*A61K 51/00* (2006.01)
*A61M 36/14* (2006.01)

(52) U.S. Cl. .................... 424/1.49; 424/1.11; 424/1.29; 424/1.81; 530/387.1

(58) Field of Classification Search ........................ None
See application file for complete search history.

(56) References Cited

PUBLICATIONS

Hawthorne et al. (Journal of Neuro-Oncolgy 2003; 62: 33-45.*
Peer et al, "Nanocarriers as an Emerging Platform for Cancer Therapy", Nature Nanotechnology, 2 (2007), pp. 751-760.

* cited by examiner

*Primary Examiner*—Misook Yu
(74) *Attorney, Agent, or Firm*—Novak Druce + Quigg LLP

(57) ABSTRACT

The present invention provides a novel approach to cancer therapy and diagnostics that utilizes nanotubes and other similar nanostructures as both an indirect source of radiation therapy (BNCT), and as delivery vehicles for other types of radio- and chemo-therapeutic materials, as well as imaging agents for diagnostic purposes.

8 Claims, 14 Drawing Sheets

A

B

A

B

A

B

A

B

A

B

A

B

A

B

NANOTUBES FOR CANCER THERAPY AND DIAGNOSTICS

CROSS-REFERENCE TO RELATED APPLICATIONS

This application is a continuation-in-part application that claims priority to U.S. Utility patent application Ser. No. 11/005,412, filed Dec. 6, 2004 now abandoned, which claims priority to U.S. Provisional Patent Application Ser. Nos. 60/527,454, filed Dec. 5, 2003; and 60/553,907, filed Mar. 17, 2004. These applications are herein incorporated by reference in their entirety.

FEDERALLY SPONSORED RESEARCH

The present invention was made with support from the United States Food and Drug Administration.

FIELD OF THE INVENTION

The present invention relates generally to cancer therapy methods, and more specifically to the use of novel nanostructure-cell-targeting species as delivery vehicles for such therapies.

BACKGROUND OF INVENTION

Radiation therapy (radiotherapy) is well-established in the treatment of cancers. Such radiation generally involves the localized delivery of radiation to the site of a tumor, wherein such radiation is generally in the form of X-rays, beta particles ($\beta^-$, i.e., electrons), gamma radiation ($\gamma$), and/or alpha particles ($\alpha$, i.e., helium nuclei). Such radiation therapy relies on the free radical disruption of cellular DNA to destroy cancer cells in a targeted manner. Radiation may come from a machine outside the body (external-beam radiation therapy), or it may come from radioactive material placed in the body near cancer cells (internal radiation therapy, implant radiation, or brachytherapy). Systemic radiation therapy uses a radioactive substance, such as a radiolabeled monoclonal antibody, that circulates throughout the body. Such internal radiation therapy (localized or systemic) typically involves a careful selection of material comprising radioactive isotopes (radioisotopes) capable of delivering the desired type and amount of radiation.

Radioisotopes also find use as medical diagnostic tools. An example of this is in positron emission tomography (PET), wherein radioisotopes capable of emitting positrons ($\beta^+$) find application. Other radioisotope-based diagnostic tools include gamma cameras and single photon emission computer tomography (SPECT). With the increasing use of radiopharmaceuticals with specific biological affinities, gamma cameras and SPECT have become increasingly important diagnostic tools. These tools have been used to image virtually every organ in the body. Brain tumors, for example, can be located by SPECT after intravenous injection of $Na^{99m}TcO_4$, as brain tumors have a very high affinity for Tc. Alzheimers disease has been studied using a gamma camera and the radioisotope $^{133}Xe$. Other radioisotopes and their medical uses include $^{133}Xe/^{99m}Tc$ for pulmonary embolism, $^{123}I/^{99m}Tc$ for renal function, and $^{201}Tl$ for cardiac infarction and ischaemia.

Boron Neutron-Capture Therapy

Boron Neutron Capture Therapy (BNCT) is an experimental approach to cancer treatment that is based on a dual-step technique: accumulation of a boron-containing compound within a tumor and treatment with a beam of low-energy neutrons directed at the boron-containing tumor. The nuclei of the boron atoms capture the neutrons and split into two highly charged particles (alpha particle and lithium ion) that have very short path lengths, approximating one cell diameter. These charged particles release sufficient energy locally to kill any tumor cells that contain high concentrations of boron. Over the past nine years, the United States Dept. of Energy (DOE) has supported a nationwide research program to develop BNCT for clinical use.

Catching Neutrons to Combat Cancer

Subjecting boron atoms to low-energy neutron radiation (thermal neutrons) causes the boron nuclei to disintegrate into alpha particles and lithium isotopes with a kinetic energy of 2.5 MeV. When this disintegration occurs in malignant cells, the energy generated is sufficient to destroy them without damaging the neighboring cells, since the range of the particles is only about 10 microns. In such BNCT, it has been estimated that it takes 109 boron atoms per tumor cell for a therapeutic dose. See Hawthorne et al., J. Neuro-Oncology, (2003) 62: 33-45. As each tumor cell has about $10^6$ effective antigenic sites that can act as targets, the number of boron atoms required per carrier has been calculated to be $10^3$. Thus, 1,000 boron atoms are needed per antibody molecule for effective treatment. However, this has been heretofore impractical because when this many small carbo-borane molecules are attached to the antibody molecule, it loses its tumor-specific targeting ability. Hawthorne et al.

Other boron-containing compounds (e.g., porphyrins containing boron) currently being used in such therapies, however, generally comprise only a very small amount of boron. It would be useful if a molecular species with a higher percentage of boron (wt. % relative to the overall molecular weight of the molecule) could be used in BNCT.

Boron Nitride Nanotubes

Boron nitride (BN) nanotubes have been synthesized and shown to behave in many ways like their carbon nanotube analogues [Chopra et al., Solid State Commun., (1998) 105: 297-300; Cumings et al., Chem. Phys. Lett., (2000) 316: 211-216]. For example, they show the same propensity to agglomerate into bundles held together by van der Waals attractive forces. Furthermore, they have been observed to exist as single- or multi-walled varieties. There are notable differences, however, namely that they are insulating and possess a constant bandgap of 5 eV irrespective of tube diameter, number of walls, and chirality [Demczyk et al., Appl. Phys. Lett., (2001) 78(18): 2772-2774; Mickelson et al., Science, (2003) 300: 467-469].

Use of such BN nanotubes (BNnt), such as those described above, in BNCT would be very advantageous on a percent boron basis—if BN nanotubes could be made therapeutically deliverable. Additionally, other types of nanotubes and nanostructures could be made to serve as delivery vehicles in cancer treatments and in diagnostic imaging. A related advantage is the ability to attach BN nanostructures to an IgG or other targeting biomolecule at only one or a few locations, so that the attached therapeutic atoms do not cover or interfere with the target molecule's receptor and thus compromise specificity.

BRIEF DESCRIPTION OF THE INVENTION

The present invention is directed to novel methods and compositions for the treatment of cancer, wherein such methods and compositions utilize nanotubes and other similar nanostructures as both an indirect source of radiation therapy, and as delivery vehicles for other types of radio- and chemotherapeutic materials, as well as imaging agents for diagnostic purposes.

Some embodiments of the present invention involve the use of BN nanostructures in boron neutron capture therapy (BNCT). In some embodiments, antibody species or other cell-targeting species are attached to the BN nanostructures to enable them to target tumors when administered to a mammalian subject. These tumor-targeting species are referred to herein as BN nanostructure-cell-targeting composite species, or if antibodies are used, BN nanostructure-antibody composite species. Once such composite species are in the proximity of a tumor, they can be activated with transdermal neutrons. Once activated, the $^{10}B$ atoms emit alpha particles that are capable of destroying cancerous cells.

In some embodiments of the present invention, carbon nanostructures (e.g., carbon nanotubes) are used to deliver radiation to a target region. In such embodiments, radioactive isotopes, such as $^{128}I$, are attached to a carbon nanostructure to which one or more antibody or cell-targeting species are attached. These radioactive-laden carbon nanotube-cell-targeting species can then be employed to selectively target tumors when administered to a mammalian subject.

In other embodiments, tumor cloned IgGs are used to carry nanocontainers (e.g., single-wall carbon nanotubes), bound to the IgGs, to the tumor sites. Ultrasonic waves are then used to explode the carbon nanotubes in the proximity of the tumor. Ultrasound is capable of penetrating deep through tissue without tissue damage because the frequency of the waves can be adjusted to be absorbed only by the target, here carbon or other nanostructures. The technique can also be used to deliver effective chemotherapeutic substances, toxic to a tumor, encapsulated inside the nanostructures.

In further embodiments of the invention, the BN nanostructures are attached to an antibody or cell-targeting species that specifically binds to the cell surfaces of tumor cells. Such surface binding can be advantageous because it may avoid cell penetration and the subsequent eliciting of undesired immune responses.

In all of the above-mentioned embodiments, the BN nanostructures, the carbon nanostructures, and the nanocontainers (nanovessels), can all be encapsulated with a bio-polymer, such as chitosan. In some of these embodiments, the antibody or cell-targeting species is attached to the nanostructure/nanocontainer through the bio-polymer. Encapsulating materials such as these with bio-polymers can circumvent the need to attach the antibody or cell-targeting species (e.g., IgG), and it can reduce potential nanoparticle toxicity and/or enhance the solubility of the IgG-nanostructure complexes in biological fluids.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 7B shows the size distribution profile for those cells. These results indicate that there were insubstantial differences in TK6 cell viability and size distribution after such treatment when compared to the control cells in FIG. 6.

FIG. 8B shows the size distribution profile for those cells. The results indicate that such treatment left very few intact TK6 cells.

DETAILED DESCRIPTION OF THE INVENTION

Figure 1:
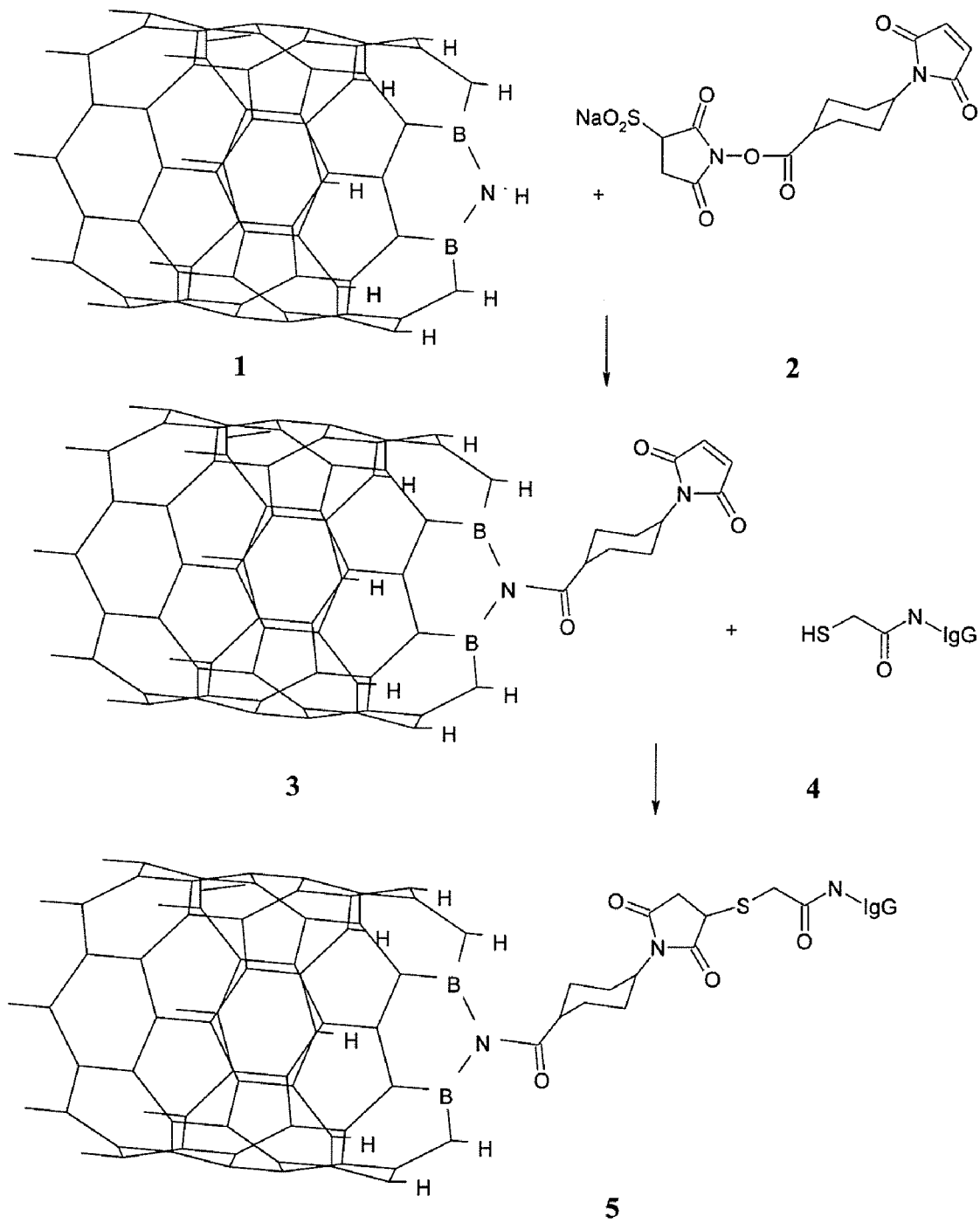
FIG. 1 illustrates, schematically, the attachment of IgG to a BN nanotube via a covalent linkage, in accordance with some embodiments of the present invention.

The present invention provides a novel approach to cancer therapy and diagnostics that utilizes nanotubes and other similar nanostructures as both an indirect source of radiation therapy (BNCT), and as delivery vehicles for other types of radio- and chemo-therapeutic materials, as well as imaging agents for diagnostic purposes.

In some embodiments of the present invention, boron-nitride (BN) nanostructures are used, particularly for BNCT. BN nanostructures, according to the present invention, include, but are not limited to, BN nanotubes, BN nanoscrolls, BN nanofibrils, BN nanovessels, BN nanocontainers, and combinations thereof. In the discussions which follow, an exemplary BN nanostructure, a BN nanotube (BNNT), will be used when describing various embodiments of the present invention. It should, however, be understood by those of skill in the art that other BN nanostructures could be utilized without departing from the spirit and scope of the present invention. In addition, BCN nanostructures (nanostructures in which a portion of the carbon atoms have been replaced by boron and nitrogen atoms) are types of BN nanostructures, which can also be used within the scope of the present invention.

BN nanotubes, according to the present invention, may comprise a variety of diameters, tube lengths, and chiralities. They may comprise one or more "walls" in their structural composition, although studies have suggested that there is a stabilizing effect for BN nanotubes comprising two walls. Further, they may be either open ended or capped, and they may be chemically functionalized on their ends, sidewalls, or both.

In some embodiments of the present invention, carbon nanostructures are employed. In the discussions which follow, an exemplary carbon nanostructure, a carbon nanotube (CNT), will be generally used when describing various embodiments of the present invention. It should, however, be understood by those of skill in the art that other carbon nanostructures could be utilized without departing from the spirit and scope of the present invention.

Carbon nanotubes, according to the present invention, include, but are not limited to, single-wall carbon nanotubes, multi-wall carbon nanotubes, double-wall carbon nanotubes, buckytubes, fullerene tubes, carbon fibrils, carbon nanotubules, carbon nanofibers, vapor-grown carbon fibers, and combination thereof. They may comprise a variety of lengths, diameters, chiralities, number of walls, and they may be either open or capped at their ends. Furthermore, they may be chemically functionalized in a variety of manners, some of which are described in Bahr et al., J. Mater. Chem., (2002) 12: 1952-1958, incorporated by reference herein.

Other nanostructures, according to the present invention, comprise nanospheres, nanoshells, nested nanoshells, nanovessels, fullerenes, nested fullerenes, nanowires, nanorods, nanococoons, and combinations thereof.

In some embodiments of the present invention, cell-targeting species, such as antibodies (including without limitation monoclonal antibodies, polyclonal antibodies, IgG's, and antibody fragments), aptamers, peptides, small molecules, and other similar molecules are employed. In more specific embodiments, tumor-cloned antibodies are employed. In the discussions which follow, exemplary tumor-cloned antibodies, such as immunoglobulins (IgGs), will be generally used when describing various embodiments of the present invention. It should, however, be understood by those of skill in the art that other suitable cell-targeting species could be utilized without departing from the spirit and scope of the present invention.

Use of Boron Nitride Nanotubes

Some embodiments of the present invention are directed to variations of boron neutron capture therapy (BNCT) using radio-activated boron-nitride (BN) nanotubes attached to tumor-cloned immunoglobulins (IgGs) or other cell-targeting species, to deliver intense, short-lived, therapeutic doses of radiation specifically to active tumor sites or disbursed metastatic cells. Such targeted delivery of nano-particles to specific types of cells has been demonstrated in the past. See, e.g., Miederer et. al., Clinical Cancer Research, (2004), 10(20): 6985; Sirdeshmukh et. al., "Functionalization of Carbon Nanotubes with Antibodies for Breast Cancer Detection Applications", Proceedings of the 2004 International Conference on MEMS, NANO and Smart Systems (ICMENS '04); Cuit et. al., Cancer Epidemiology Biomarkers & Prevention, (2004), 13:1136-1145; Chen et. al., Molecular Immunology (2004), 41(12):1247-1252; Hood et. al., Science, (2002), 296 (5577):2404-7; Hood et. al., Cold Spring Harb Symp Quant Biol., (2002), 67:285-91; De Menezes et. al., "In vitro and in vivo targeting of immunoliposomal doxorubicin to human B-cell lymphoma" Cancer Res. (1998), 58:3320-3330; Park et. al. "Anti-HER2 immunoliposomes: enhanced efficacy attributable to targeted delivery" Clin. Cancer Res. (2002), 8:1172-1181 (2002); Allen et. al., "Ligand targeting therapeutics in anticancer therapy" Nat. Res. Cancer (2002), 2:750-763.

In the present invention, a nanotube and IgG (or other cell-targeting species) are attached if they remain associated with one another such that the therapeutic dose is delivered to the targeted active tumor sites. In some embodiments, this attachment is a covalent-type bonding, and the resulting molecular composite termed a BN nanotube-immunoglobulin (BNNT-IgGs) species.

BNCT is a technique that relies on (non-radioactive) $^{10}$B being delivered specifically to a tumor site, and then activating it using an accurate beam of epithermal neutrons, which are low energy neutrons with velocities adjusted to penetrate tissue to the specific tumor depth, where the $^{10}$B has lodged.

A BN nanotube's structure is similar to the "rolled-up-graphite" structure of a carbon nanotube; six-membered rings, but with boron atoms being singly bound to 3 surrounding nitrogen atoms, and the nitrogen atoms bound to surrounding boron atoms (no conjugation). Thus, each BN nanotube is composed of a substantial number of boron atoms, i.e., 50%, meaning hundreds to thousands for each nanotube.

Boron has a relatively large radioactive cross section and so can be easily made radioactive in a neutron flux. Radioactive boron is an alpha and gamma emitter with isotopes of $^{12}$B and $^{13}$B, having γ energies of 4.439 MeV and 3.68 MeV, respectively. The alpha particles may or may not have enough energy to kill cells unless the nanotubes actually penetrate the cell walls through the unattached ends. The gamma rays should do enough damage for therapy, especially since there will be many generated from the multitude of boron atoms associated with the BN nanotubes. There will also be a local toxic effect from a lithium ion produced as each radioactive boron atom decays. In an aqueous environment, Li$^+$ should produce LiOH, a very strong base, which can do a lot of damage to cancer cells, but is likely to be rapidly diluted in any aqueous body fluids or media (cellular fluids as well as plasma). Thus, using the BNnt-IgGs species in BNCT, it is possible to deliver a highly concentrated dose of radiation precursor (boron) to intended targets (tumors or individual cancer cells) with great specificity.

Referring to FIG. 1, in some embodiments of the present invention, covalent attachment of the BN nanotubes to the IgG relies on the terminal nitrogen atoms of each tube, themselves terminated with hydrogen, and can be accomplished using a linker reaction described previously for linking antibodies to surfaces through secondary amine linkages [Immobilized Affinity Ligand Techniques, Hermanson et al., Eds., Academic Press, New York: 1992, p. 45, incorporated herein by reference], wherein BN nanotube 1 is reacted with Sulfo-succinimidyl 4-[N-maleimidomethyl]cyclohexane-1-carboxylate (Sulfo-SMCC) 2 to yield intermediate product 3, which in turn is reacted with sulfhydral functionalized IgG 4 to yield BN nanotube-IgG composite species 5.

The chemistry illustrated in FIG. 1 is not the only type of linker chemistry, only an example. Such linker chemistry can be optimized with respect to the inherent reactivity of the BN nanotube terminal NH moiety. While not intending to be bound by theory, the reactivity of the nanotube terminal NH group is believed to be similar to a normal small molecule NH group. If the BN nanotube diameter is too small, ring strain may exist in the BN structure. In this situation attachment of the Sulfo-SMCC molecule to form intermediate product 3 may create small aberrations in the ring structure, lead to tube fracture, and possibly even substitution in the internal portions of the ring-system. It is envisioned that, in some embodiments, more than one BN nanotube is attached to an IgG molecule (or other cell-targeting species). In other embodiments, multiple IgG molecules (or other cell-targeting species) are attached to a single BN nanotube. In some embodiments, there may be multiple linkers between the BN nanotube and the IgG (or other cell-targeting species).

In some embodiments, there may be issues that have to be overcome to get BN nanotubes into solution. These issues may be solved (at least in part) by reducing the size (width and length) of the BN nanotubes. In some embodiments, solubility issues can be overcome via chemical functionalization and/or other modification of the BN nanotubes. For example, it may also be possible to put propylene glycol or other polar groups on the BN nanotube ends to improve BN nanotube salvation. In some embodiments, surfactants may be employed to facilitate solubility.

The therapy will involve activation of the BN nanotubes with a neutron beam (as in BNCT) once the IgG carrier molecules have reached their target tissue. This invention addresses three limitations in the present art of BNCT: (1) specificity, meaning the ability to target accurately the tumor tissue, (2) the amount of radiation, that is, how many boron atoms can be delivered to the tumor site, and (3) non-applicability for metastasized cells, resolvable by this invention because the vast number of boron atoms per nanotube can accelerate achievement of a local therapeutic dose and allow meaningful large area (even whole body) neutron activation strategies. Most molecules that are currently used by BNCT can only deliver one or two boron atoms per molecule and do so without the cancer cell target specificity associated with an IgG. Thus, BNCT is only as specific as the columnation of the neutron-activating beam allows. The present invention, using BN nanotubes can deliver significant numbers of boron atoms (100s to 1000s) specifically to the tumor site while avoiding exposures to surrounding tissue.

In other embodiments, the present invention can also provide an advantage in minimizing the body's undesired immune responses to BNCT. For instance, when the BN nanostructures are attached to an antibody species that specifically binds to the cell surface of tumor cells, it may avoid penetrating the cell to elicit undesired immune responses. Furthermore, BNNT's of the present invention are not expected to elicit substantial immune responses in the body due to the absence of any known antigenic epitopes on their surfaces.

Methods of activating BN nanotubes with a neutron beam, in accordance with embodiments of the present invention pertaining to BNCT, include, but are not limited to, neutron activation. Neutron activation is a process where a material placed in a neutron flux absorbs neutrons in proportion to its neutron activation cross section. The thermal neutron activation cross section ($\sigma_a$) is a number experimentally measured, which is proportional to how "sensitive" an atom is to absorbing neutrons. The unit of measurement, called a Barn, is equal to $10^{-28}$ m$^2$. When an atom absorbs a neutron, it will be transformed to an isotope of the same element, but one atomic mass unit higher. This usually results in the new isotope being radioactive. Common reactions observed with neutron activation are (n,$\gamma$), (n,p), and (n,$\alpha$). This notation indicates that a neutron is being absorbed by a particular nuclei and a gamma ray, proton or alpha particle is being expelled, respectively. The BNCT described herein involves $^{10}$B, which is given by $^{10}$B(n,$\alpha$)$^7$Li, where $^{10}$B ($\sigma_a$=3838 Barns) is being activated by a neutron and an alpha ($\alpha$) particle is ejected with the result that a $^7$Li is produced. This is the most common reaction with the isotope $^{10}$B, and it is practically instantaneous.

In the present invention, various devices can be used to activate BN nanotubes. Non-limiting examples of such devices include reactors, radio-isotopes, and accelerators. An example of an accelerator that may be suitable for use in the present invention is the P 211 Neutron Generator by Thermo Scientific.

Furthermore, by using BNNT attached to a cell-targeting species (such as BNNT-IgGs species), this allows for whole body BNCT treatment in which the whole body being treated can be radioactivated with a diffuse epithermal neutron beam. Through the use of the cell-targeting species, the disclosed BNNT-based therapy confers cell-level specificity. The boron atom load of the BNNT is sufficiently concentrated that effective dosing is possible with a much shorter activation time in any one region of the body. Such a process can be used in combination with more aggressive activation on specific target sites. For instance, identified tumors can first be targeted with one level of activation, followed by a lighter dose of neutrons for remaining parts of the body.

While the embodiments described above have been directed primarily at targeting identified tumor cell with a high degree of specificity, diffuse neutron beams can be employed in volumes around the periphery of tumor masses, along lymph ducts and in the glands, and even in whole-body irradiation therapies. Such embodiments would allow for the destruction even of metastasized cells.

Use of Carbon Nanostructures

In some embodiments of this invention, tumor cloned IgGs (or other cell-targeting species) are utilized to carry carbon nanostructures (e.g. carbon nanotubes) that are attached to the IgGs, and that carry a substantial amount of radioactive material specifically to tumor sites. Such nanostructure-IgG composites comprising a radioactive material are termed radioactive nanostructure-IgG species. When the nanostructure is a carbon nanotube, the radioactive nanostructure-IgG species is termed a radioactive CNT-IgG species. In some embodiments, the carbon nanotube (CNT) attachment to the IgG comprises covalent bonding, as described above for BN nanotubes, using known linker chemistry for CNTs. See Liu et al., Science, (1998) 280: 1253-1256, incorporated herein by reference.

The radioactive material carried by the nanostructure can be atomic or molecular in nature, and can be attached to the nanostructure before or after the nanostructure is attached to the IgG or other cell-targeting species. Generally, this radioactive material can be any radioactive isotope or isotopes currently used in the medical treatment of cancer. In some embodiments, this radioactive material is an iodine isotope. Such an isotope can be present as a salt (e.g., $PbI_2$). An exemplary iodine isotope is $^{128}I$, which has a half-life of 25 minutes ($t_{1/2}$=25 min). Furthermore, since the IgGs carry the radioactive species before they reach the tumor site, in some embodiments, the IgGs can also hunt down metastasized cells in the body as they are recognized. This is similar in concept to the above-described BNCT embodiments, except that instead of activating the radioactive species at the tumor site, the species will be radioactive before the IgGs are introduced into the body. This is feasible because the $^{128}I$ has a 25-minute half-life whereas the radioactive boron nuclei (generated in situ) have microsecond half-lives. Other radioactive species could be used besides $^{128}I$. Other suitable radionuclei that can be employed depending upon the type of radiation desired, the intensity, and the duration (controlled by the half-life) include, but are not limited to, $^{121}I$ ($t_{1/2}$=2.12 hours), $^{124}I$ ($t_{1/2}$=4.17 days), $^{131}I$ ($t_{1/2}$=8.0 days), $^{133}I$ ($t_{1/2}$=20.8 hours), $^{135}I$ ($t_{1/2}$=6.58 hours), isotopes of Tellurium, and combinations thereof. Essentially, any therapeutically-suitable radioisotope which can be attached to a nanostructure, which in turn can be attached to an IgG (or other cell-targeting species), can be used (CNT-antibody linker chemistry is well established in the scientific literature). Examples of radioactive isotopes commonly used in medical applications are shown in Table 1.

TABLE 1

| Isotope | Radiation type | Half-life ($t_{1/2}$) | Source (typical) | Use (typical) |
| --- | --- | --- | --- | --- |
| $^{99}Mo$ | $\beta^-$ | 65.94 hours | Nuclear reactor | Parent of $^{99m}Tc$ |
| $^{99m}Tc$ | Isomeric transition, $\gamma$ | 6.01 hours | Nuclear reactor | Diagnostic |
| $^{60}Cr$ | $\beta^-$ | 0.6 sec | Nuclear reactor | Diagnostic |
| $^{192}Ir$ | $\beta^-$ | 73.83 days | Nuclear reactor | Therapeutic |
| $^{32}P$ | $\beta^-$ | 14.28 days | Nuclear reactor | Therapeutic |
| $^{89}Sr$ | $\beta^-$ | 50.52 days | Nuclear reactor | Therapeutic |
| $^{90}Y$ | $\beta^-$ | 64.0 hours | Nuclear reactor | Therapeutic |
| $^{153}Sm$ | $\beta^-$ | 46.7 hours | Nuclear reactor | Therapeutic |
| $^{67}Ga$ | Orbital electron capture, $\gamma$ | 78.25 hours | Cyclotron | Diagnostic |
| $^{201}Tl$ | Orbital electron capture, $\gamma$ | 3.05 days | Cyclotron | Diagnostic |
| $^{123}I$ | Orbital electron capture, $\gamma$ | 13.1 hours | Cyclotron | Diagnostic |

Figure 2:
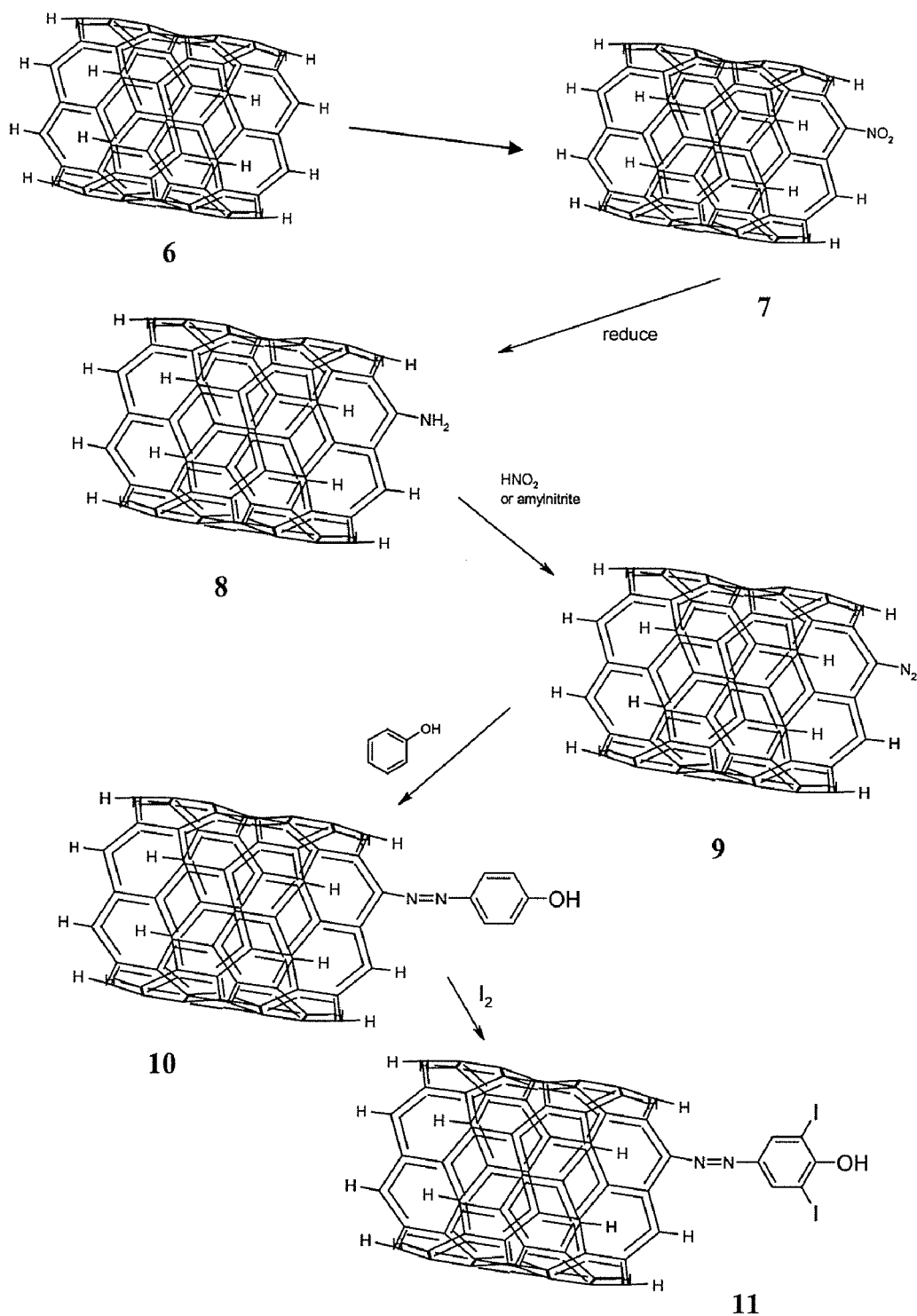
FIG. 2 illustrates, schematically, an embodiment of the present invention, wherein iodine-bearing moieties are covalently attached to carbon nanotubes, and wherein at least some of the iodine emits radiation of a therapeutic kind.

The number of radioactive nuclei delivered in such a manner by each CNT can vary from a single atom to thousands, depending on how much is desired and the manner in which the radioactive nuclei are attached to the CNT. Furthermore, the manner in which the radioisotope atoms are attached to the CNT can be of a covalent and/or physisorptive nature. In some embodiments, this is an intercalation process. Numerous methods exist for attaching such radioactive species to CNTs. Shown in FIG. 2 are some exemplary methods of attaching iodine to CNTs based on a non-traditional nitration of 6 to 7. See Korfmacher et al., J. High Resolut. Chrom. Commun., (1984) 7: 581-583; and Miller et al., J. Org. Chem., (1992) 57: 3746-3748. The reaction scheme ultimately leads to 11 with radioactive iodine attached to the end of the CNT.

In some embodiments, the radioisotope atoms (or molecules) are activated (i.e., generated) before being attached to the CNTs, whereas in other embodiments, they are activated post-attachment. One exemplary method of radioisotope activation comprises the laser-driven photo-transmutation of $^{129}I$ (a long-lived nuclear waste product) to $^{128}I$ by irradiating a gold target with laser pulses from a Nd:glass laser with wavelength $\lambda$~1 micron. Relativistic electrons from the ensuing hot plasma are converted to high-energy bremsstrahlung in the target. The gamma radiation from the target induces transmutation of the iodine samples through ($\gamma$, n) reactions [see Ledingham et al., J. Phys. D: Appl. Phys., (2003) 36: L79-L82, incorporated herein by reference]. Other forms of gamma radiation (e.g., $^{60}Co$) may also be used to carry out such a transmutation. Alternatively, neutron activation may be used.

Because the radioactive atoms (or molecules) are activated before treatment, no subsequent activation is required once the IgG carrier molecules have reached their target tissue, such as discussed above for the BNNT and IgG method described above. In some embodiments, this allows for the targeting of individual molecules that are located outside of tumor sites. For instance, a target molecule located within the bloodstream can be a target for the radioactive CNT-IgG species.

Use of Nanovessels

In some embodiments of the present invention, tumor cloned IgGs or other cell-targeting species are used to carry nanocontainers, probably single walled nanovessels (e.g., single-wall carbon nanotubes), covalently bound to the cell-targeting species, to the tumor sites. As mentioned previously, such targeted delivery of nano-particles to specific types of cells has been demonstrated in the past.

In further embodiments, ultrasound waves with a frequency that is absorbed by the nanotubes (~20-40 KHz), can then be used to explode the carbon nanotubes in the proximity of the tumor. Such use of ultrasound waves to explode carbon nanotubes is analogous to the ultrasound method that is used to destroy kidney stones. Ultrasound is capable of penetrating deep through tissue without tissue damage because the frequency of the waves can be adjusted to be absorbed only by the target, here carbon or other nanostructures. The technique can also be used to deliver effective chemotherapeutic substances, toxic to a tumor, encapsulated inside the nanostructures. Some examples of toxic materials are inorganic substances such as arsenic oxide (AsO), cadmium, cisplatin, etc., as well as organic chemotherapeutic agents such as vinblastine/vincristine, ifosfamide, etoposide, etc. Unfortunately, while these chemotherapeutic agents are very effective at destroying cells through various mechanisms, they do not discriminate between healthy cells and tumor cells. This can result in the severe side effects that are associated with conventional chemotherapy. However, by using IgGs or other cell-targeting species to deliver drug-filled nanostructures directly to a tumor, then using ultrasonic waves to break open the nanostructures and release the tumor-toxic substances at the site of the tumor, many of the side effects can be reduced or eliminated. In each case, the cell-targeting species are used to carry nanostructures specifically to a tumor, and ultrasonic waves are used to either explode or break open the nanotubes, destroying the tumor.

As discussed above, a practical aspect surrounding certain embodiments of the present invention is the use of covalently-linked IgG targeting. In such case, it is believed that there may be advantages in separating, prior to injection into a patient, the non-linked nanotubes from those that have been successfully linked. This can be accomplished rapidly using separation techniques such as field flow fractionation, size exclusion chromatography, differential centrifugation, etc. To reduce sample volume following separation, liquid-liquid extraction, electrostatic precipitation, centrifugation with decanting, or filtering may be required. It is believed that any non-targeted toxicity from nanoscale particles interacting with normal tissue will be avoided if the only injected nanoparticles are covalently bound to IgGs, which are much larger, protein-scale entities.

Use of Encapsulation

Figure 3:
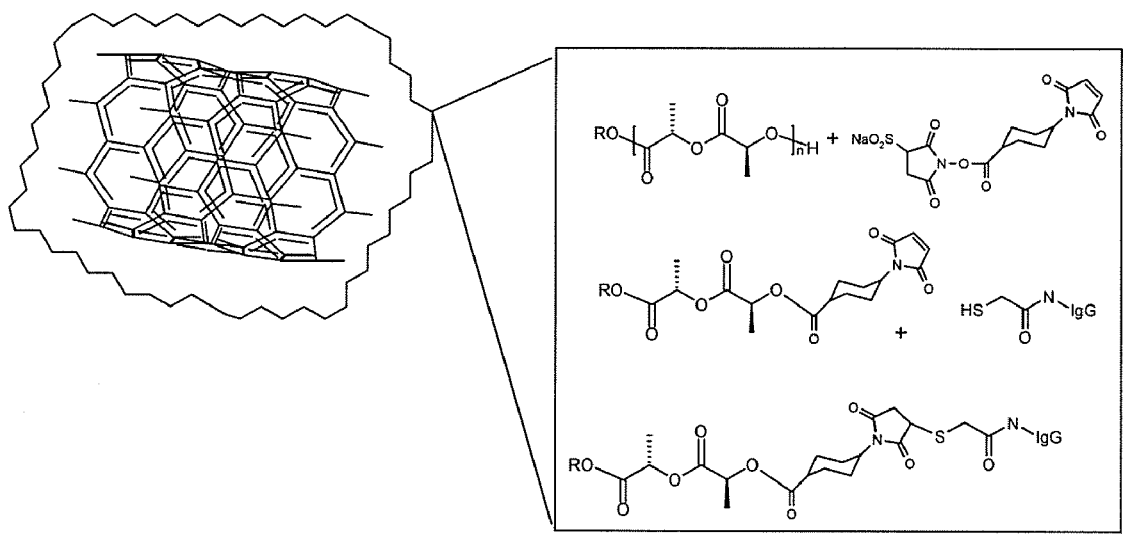
FIG. 3 illustrates embodiments of the present invention wherein the nanostructures are encapsulated with polylactic acid (an exemplary bio-polymer) and covalently bound to an IgG through the reaction detailed in the box.

In some embodiments of the invention, polymers or bio-polymers can be used to encapsulate the BN, BCN, and CNT nanostructures. For example the bio-polymer polylactic acid can be used to encapsulate the nanostructures—which can be further functionalized and covalently linked to IgG. This can circumvent having to link the IgG to the nanostructures directly. FIG. 3 illustrates of the embodiments described above. The chemistry depicted in FIG. 3 is only an example of linker chemistry for polylactic acid capsule-IgG binding and is not the only type of linker chemistry. For example, polylactic acid of approximately 120,000 $M_w$ mol weight can be obtained in 30 min in solvents such as methylene chloride and ethyl acetate (Macromol. Rapid Commun. 25, 1402, 2004). Polylactic acid possesses a lipophilic character that may enhance its ability to pass through a cell membrane.

Another example of a bio-polymer that could be used to encapsulate the nanostructures is polyaspartic acid. Polyaspartic acid, which contains an amide linkage, a terminal amine, and multiple carboxylic acids for favorable solvent polarity, can also be used to encapsulate nanoparticles. Encapsulating materials such as these bio-polymers reduce potential nanoparticle toxicity and enhance the solubility of the IgG-nanostructure complexes in biological fluids.

Another example of a bio-polymer that can be used to encapsulate the nanostructures of the present invention is Chitosan. Chitosan generally refers to a linear polysaccharide with randomly distributed β-(1-4)-linked D-glucosamine and N-acetyl-D-glucosamine. The amino groups in chitosan have pKa values of approximately 6.5. Thus, chitosan can be positively charged in acidic to neutral solutions. These properties can make chitosan bioadhesive such that it can readily bind to negatively charged surfaces. In addition, Chitosan is generally biocompatible and biodegradable. Even more advantageously, Chitosan can be insoluble in water and many PBS buffers, but still reactive towards functional groups. Thus, it is envisioned that BN nanotubes with Chitosan coatings can be readily coupled to functionalized antibody molecules without requiring dissolution.

It is also envisioned that chitosan can be used safely and effectively with the nano-particles of the present invention. For instance, a study demonstrated that chitosan does not elicit a significant immune response in mice. Vila et. al., Eur J Pharm Biopharm. (2004), 57(1):123-31. In addition, Chitosan-coated nanoparticles have been used in conjunction with luminescent semiconductor quantum dots and evaluated for use in bio-imaging. Nie et al, Nanotechnology. 2006. 17:140-44.

Various microencapsulation methods can be used to achieve encapsulation of the nanostructures by the bio-polymers. Examples of these methods include, but are not limited to, emulsification methods, electrospray techniques, and potentially ultrasonic nebulization. Each method can present various advantages. For instance, under an electrospray approach, the sprayed droplets would dry due to their low volatility residues before hitting a surface such that the resulting residues from each droplet would contain one or more nanostructure with a dried coating. In one embodiment, the electrospray solution can include chitosan. In another embodiment, chitosan can be used in conjunction with a Zn-containing compound, such as Zn-porphyrin or Zn-phthalocyanine. Without being bound by theory, such Zn containing compounds can help solubilize the compounds of the present invention before electrospray treatment. For instance, Zn-phthalocyanine has been reported to water-solubilize BNNTs. See, e.g., Qing Huang et. al. "Donor-Acceptor Nanoensembles Based on Boron Nitride Nanotubes" *Adv. Mater.* 2007, 19, 934-938.

Embodiments of the present invention encompass the use of any technique that produces a thin coating of the nanostructure, where the coating can be used to improve membrane passage or other physico/chemical characteristics of the nanostructure, to reduce incidental or unintended toxicity of the nanostructure, and/or to facilitate irreversible attachment of the nanostructure to an IgG, antibody, or other cell-targeting species.

Many variations exist for this invention. The chemistry for attachment of BN nanotubes and carbon nanotubes to the IgGs can be optimized for particular therapies. The number of nanotubes that can be covalently bonded to each IgG can be varied. The size of the nanotubes (either BN or carbon) attached to each IgG can be varied. The frequency of the ultrasound waves used to explode or break open nanotubes can be varied to produce a variety of outcomes for a variety of structures.

In addition to the therapeutic methods made possible by the present invention, nanotubes and nanovessels, comprising atoms and/or molecules with suitable nuclei and linked with one or more IgGs, can be used in the diagnostic imaging of tumors.

Recently, Applicants have discovered that cancer cells seem to die in the presence of carbon nanofibers, while non-cancerous cells are unaffected. Thus, the present invention is also directed to methods by which carbon nanofibers linked to IgG molecules are delivered to cancer cells for the purpose of killing them without using any radioisotope, chemical agent, or intentional physical disruption of targeted cells.

Further, any or all of the abovementioned therapies may be employed for a single patient for a given set of circumstances (e.g., combination therapies). These therapies can be performed sequentially or simultaneously. For instance, the BNNT-IgG therapy can be performed first, followed by the radioactive CNT-IgG therapy. In such combination therapies, the IgGs utilized during each can be the same or, alternatively, different IgGs for each therapy. Since the different IgGs can be selected to attach to different portions of the targeted specie, it is believed that there may be some advantage to using different IgGs during combination therapies.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

Example 1

This Example serves to illustrate, by way of a calculation, the efficiency by which BN nanotubes can deliver radiation to a tumor site in BNCT. A 1 µg amount of BNnt is shown to locally deliver 0.43 microcuries (µc).

---

$$N = \frac{\phi V \sum_a}{\lambda}(1 - e^{-\lambda t})$$

$$\overline{\sigma}_{a1} = \sigma_{a298}\left(\frac{\sqrt{\pi}}{2}\right)\sqrt{\frac{293}{T}}$$

$A_0 = N_1\lambda_1 + N_2\lambda_2 \quad = (\sigma_a{}^\alpha)(0.868) \qquad {}^{19.9\%}_{10}B \Rightarrow \sigma_a^\alpha = 3838\,b$ $N_1\lambda_1 = \sigma'_{a1}N_0\phi \quad = (3{,}838\,b)(0.868)$ $N_2\lambda_2 = \sigma'_{a2}N_0\phi \quad \begin{aligned}&= 3{,}332.5\,b \\ &= 3332.5 \times 10^{-24}\,\text{cm}^2\end{aligned} \qquad {}^{80.0\%}_{11}B \Rightarrow \sigma_a^\alpha = 5\,\text{mb}$ \# boron atoms in 0.001 grams BN nanotubes     neutrons/s $$A_0 = \frac{(3332.5 \times 10^{-24}\,\text{cm}^2)(2.4 \times 10^{16})(1 \times 10^9)}{3.7 \times 10^4\,\text{dps/µc}}$$

% activated $t_{1/2} = \dfrac{0.693}{\lambda} = (2.16\,\mu c)(0.20)$ $\qquad\qquad = 0.43\,\mu c$ (for 0.001 g of BN nanotubes delivered)

where:
N is the number of radioactive nuclei activated by the neutron beam.
φ = neutron flux
V = volume of targeted atoms
σ = sum of all nuclei which can be activated
λ = decay constant
T = time of activation

---

Example 2

This Example serves to illustrate the efficiency by which radioactive-laden CNT-IgG species can deliver radiation. In the calculation below, each 1 µg of CNTs administered to a mammalian subject, wherein each CNT carries only 1 $^{128}$I atoms, it is believed at least about 3 curies of radiation is delivered.

---

$^{128}_{53}\text{I} \rightarrow {}^{128}\text{Xe} + \beta^{-1} + \alpha$ $N = N_0 e^{-\lambda t}$
$A = \lambda N = \lambda N_0 e^{-\lambda t}$ $\lambda = \dfrac{\ln 2}{t_{1/2}} = \dfrac{0.693}{25\,\text{min}} = 0.027721\,\text{min}^{-1}$ MW of 100 C atom nanotube with 10 $^{128}$I per nanotube: ≈2600 g/mol

---

If 0.001 grams of nanotubes are delivered: $\dfrac{0.001\,\text{g}}{2600\,\text{g/mol}} = 3.8 \times 10^{-7}$ moles nanotubes MW of 1000 C atom nanotube with 10 $^{128}$I per nanotube: ≈14,480 g/mol $\dfrac{0.001\,\text{g}}{14{,}480\,\text{g/mol}} = 6.9 \times 10^{-8}$ moles nanotubes $N_0 = (6.91 \times 10^{-8}\,\text{moles})(6.02 \times 10^{23})$
$\qquad = 4.157 \times 10^{16}$ I atoms per 0.001 grams of 1000 C atom nanotube or
$2.318 \times 10^{17}$ I atoms per 0.001 grams of 100 C atom nanotube $A = \lambda N = (0.0277\,\text{min}^{-1})(4.157 \times 10^{16}\,\text{I atoms})(e^{-0.02772})$
$\qquad = 1.12 \times 10^{15}$ dpm = 30,270 Curies/mole of 1000 C atom nanotube however,
after 1 min → = 3 curies per 1 µg of 1 I atom per 1000 C atom nanotube
and → = 33 curies per 1 µg of 1 I atom per 100 C atom nanotube

---

Example 3

Preparation and Analysis of BN Nanotubes

BNNTs were purchased from Australian National University (Canberra, Australia). Before use, the BN nanotubes were sterilized at 75° C. for 45 minutes. Next, 1 mg aliquots were weighed and transferred into 200 mL of filter-sterilized PBS solutions in polypropylene vials.

Figure 4:
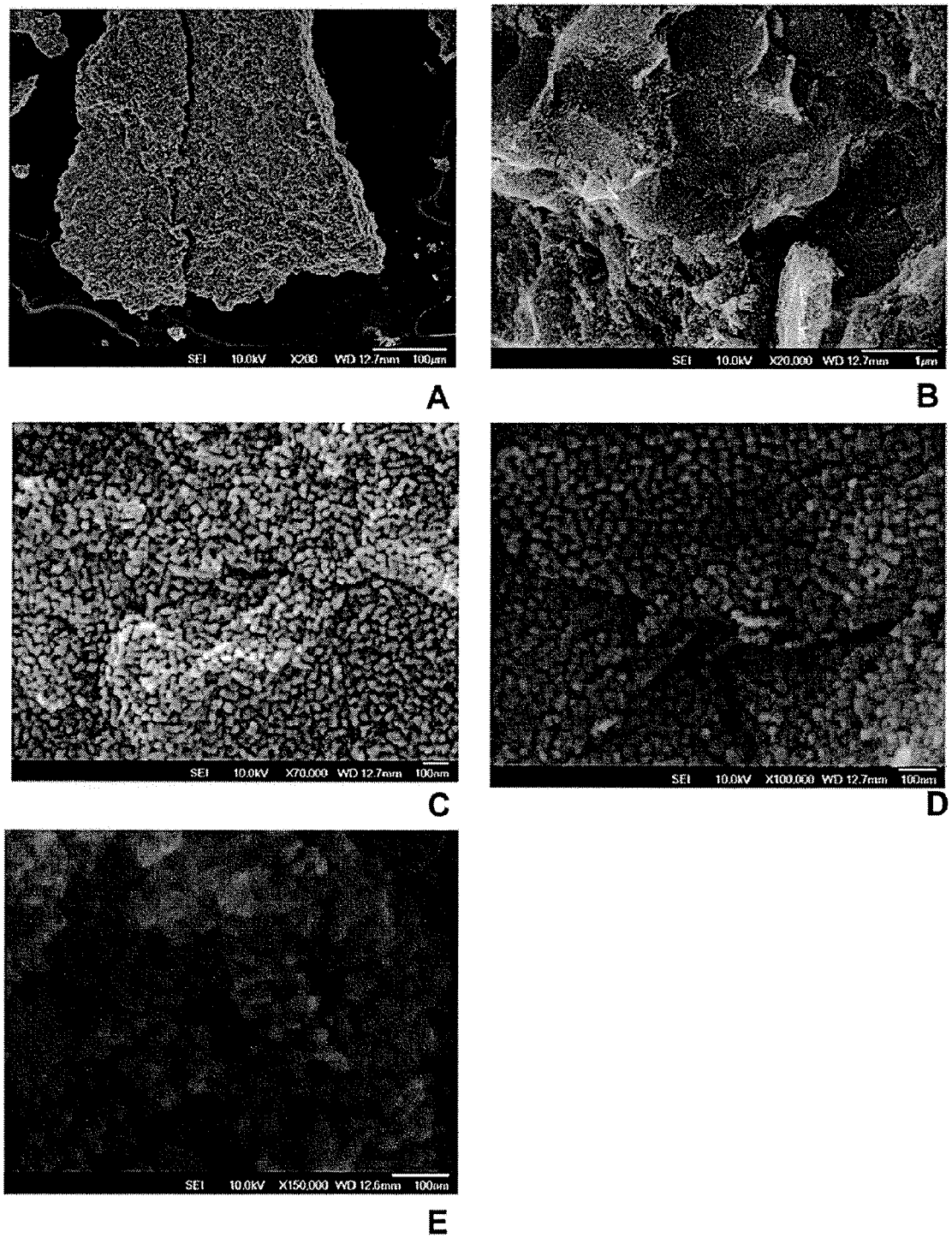
FIG. 4 shows scanning electron micrograph (SEM) images of BN nanotubes at different magnifications. The magnifications are at 200× (4A), 20,000× (4B), 70,000× (4C), 100,000× (4D), and 150,000× (4E). The BN nanotubes appear to be cylindrical solids of approximately 10 nm in diameter and 20 nm in length.

The BN nanotubes were also analyzed by scanning electron microscopy (SEM). FIG. 4 shows various SEM images of the nanotubes at different magnifications. As shown in the images, the BN nanotubes appear to be cylindrical solids of approximately 10 nm in diameter and 20 nm in length. Such a compact size can be advantageous by facilitating travel through the blood stream. Furthermore, the compact size can help facilitate the elimination of the BN nanotubes from the body once they have served their therapeutic function.

Example 4

Growth of TK6 Tumor Cells for use in BNCT Experiments

TK6 HPRT-deleted lymphoblastoid cells (human spleen) were cultured at 37° C. in a 5% $CO_2$ environment in 1 L of medium. The medium contained about 70 ml of RPM1 I640 (with L-glutamine and other essential nutrients), 25 ml of 1M HEPES (to a final conc. 25 mM), 100 ml of heat inactivated (56° C. for 30 min) fetal bovine serum (FBS, 10% final concentration), and 5 ml of a penicillin/streptomycin standard stock solution (to final concentrations of 50 mg/ml penicillin G sodium and 50 mg/ml streptomycin sulfate).

Cells were allowed to grow in the above medium for about two days. At that time, the cell count reached about $0.5 \times 10^6$ cells per ml. In addition, flow cytometry-based viability assays indicated that about 88% of the TK6 cells were still alive. Thereafter, the cell suspensions were dispensed in 1.5 ml aliquots under aseptic conditions into 2 ml polypropylene vials. The vials were then transported over ice (cool, not frozen) to Oak Ridge National Laboratory's High Flux Isotope Reactor (HFIR) for experiments.

Example 5

Efficacy of BN Nanotubes in Killing TK6 Tumor Cells

About 1 mg of the previously prepared BN nanotube mixtures were pipetted into polypropylene sample vials that contained 1.5 ml of TK6 cells. Immediately thereafter, the polypropylene vials were placed in a plastic tube rack that faced a 0.025 eV monochromatic neutron beam. The neutron beam was then applied to the cells in each vial at $10^7/cm^2$-second for 60 seconds. Control vials that contained cell suspensions without BN nanotubes were also exposed to neutron beams by the same method.

Figure 5:
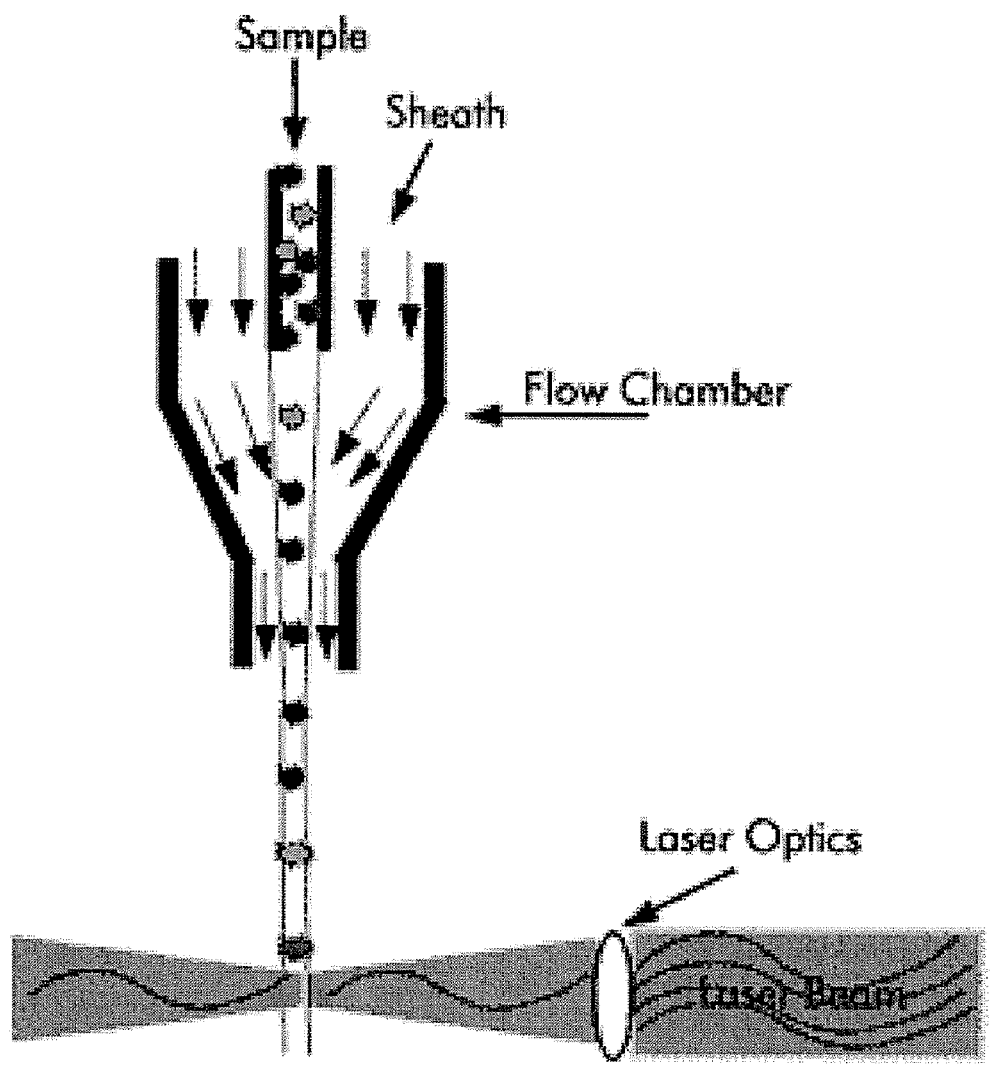
FIG. 5 illustrates a scheme of a flow cytometry-based viability assay used to assess the viability of cells after BNCT under various conditions.

The viability and size distribution of the cells were determined immediately after neutron beam treatment by a two-color viability assay that utilized a Beckman Coulter Quanta model SC flow cytometer. FIG. 5 depicts the scheme used for this flow cytometry assay. Briefly, 200 mL of a dye solution was added to each sample. The dye solution comprised thiazole orange (TO, 420 nM), propidium iodide (PI, 17.2 µM), and EDTA (1 mM) in 1×PBS. The cell suspensions were then mixed on a vortexer for 60 seconds at low energy. Next, about 100 µl of each sample was injected into the flow cytometer by a syringe for measurements.

By way of background, and without being bound by theory, it is envisioned that the TO dye in the dye solution penetrates into living (viable) cells, intercolates with DNA and yields a concentrated fluorescence in the FL1 region (525 nm) of a typical flow cytometer. Likewise, it is envisioned that the EDTA solution serves to swell the cells without rupturing their membranes in order to facilitate TO penetration. It is also envisioned that the PI dye acts in the same manner. However, since the PI dye is not substantially membrane permeable, it mainly penetrates non-viable cells, most of which have membranes that are compromised. Accordingly, it is envisioned that the PI quenches fluorescence of the TO and yields its own fluorescence in the FL3 channel (>600 nm). Therefore, by observing the color and intensity of particle fluorescence in these channels, it is possible to count cells and determine whether they are viable.

Another feature of the flow cytometric assay is that the reflected signals (scattered light of the original source color: here blue, 490 nm) from the cells can be used to characterize the cells based on their size and granularity. Therefore, it is possible to distinguish signals from non-cellular and cellular material. This is done before assessing their fluorescence by sequential gating steps built into the cytometer data acquisition protocol.

Figure 6:
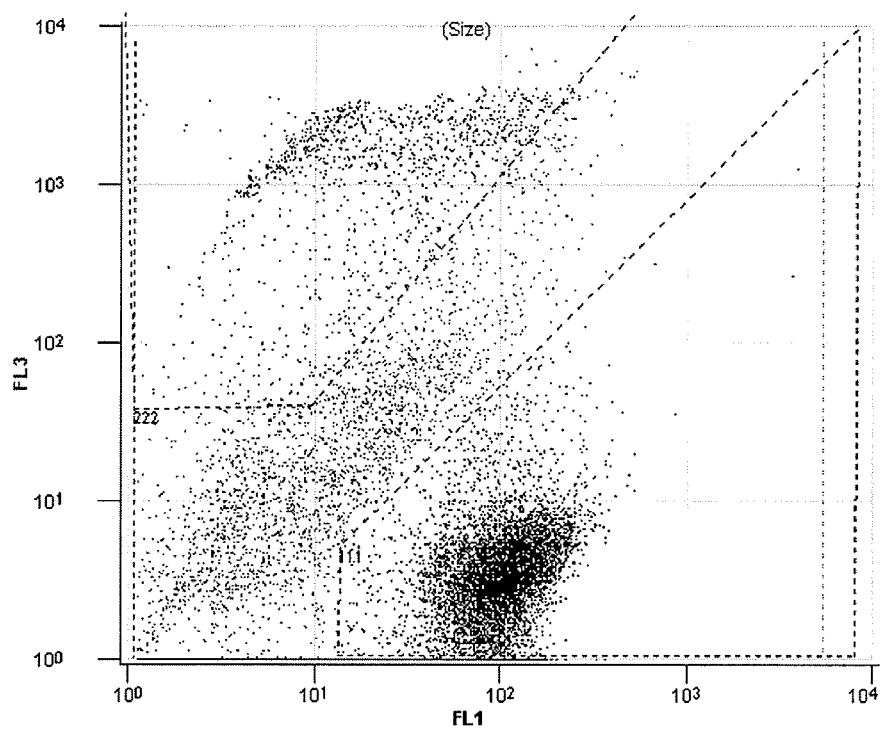
FIG. 6A shows the fluorescence activated cell sorting (FACS) profile for untreated TK6 lymphoblastoma cells.
FIG. 6B shows the size distribution profile for those cells.
Figure 6:
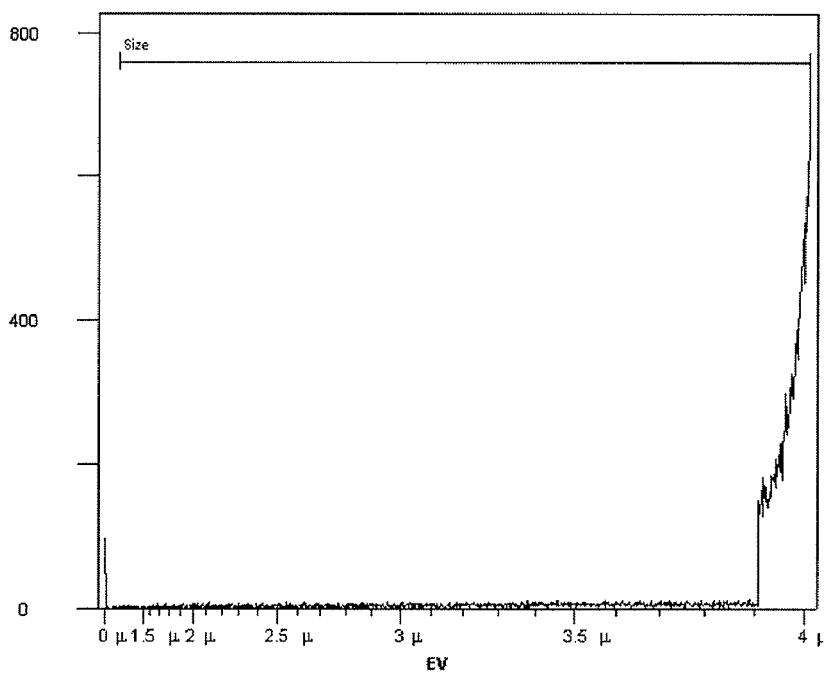

As shown in FIG. 6A and Table 2 below, unexposed and untreated TK6 cells showed good viability. In addition, as shown in FIG. 6B, the control TK6 lymphoblastoma cells were very large, and fragments were not observed, even from dead cells.

TABLE 2

Viability and Size Distribution of Control TK6 Cells

| Region | FL1 Mean | FL3 Mean | FL1 CV | Pct Gated | Pct Total | Count |
|---|---|---|---|---|---|---|
| Size | 50.0 | 90.8 | 129.28% | 99.58% | 99.58% | 25,201 |
| 111 (live) | 111.5 | 4.94 | 72.85% | 28.01% | 27.90% | 7,060 |
| 222 (dead) | 36.7 | 1,547.6 | 116.80% | 4.97% | 4.95% | 1,252 |

Figure 7:
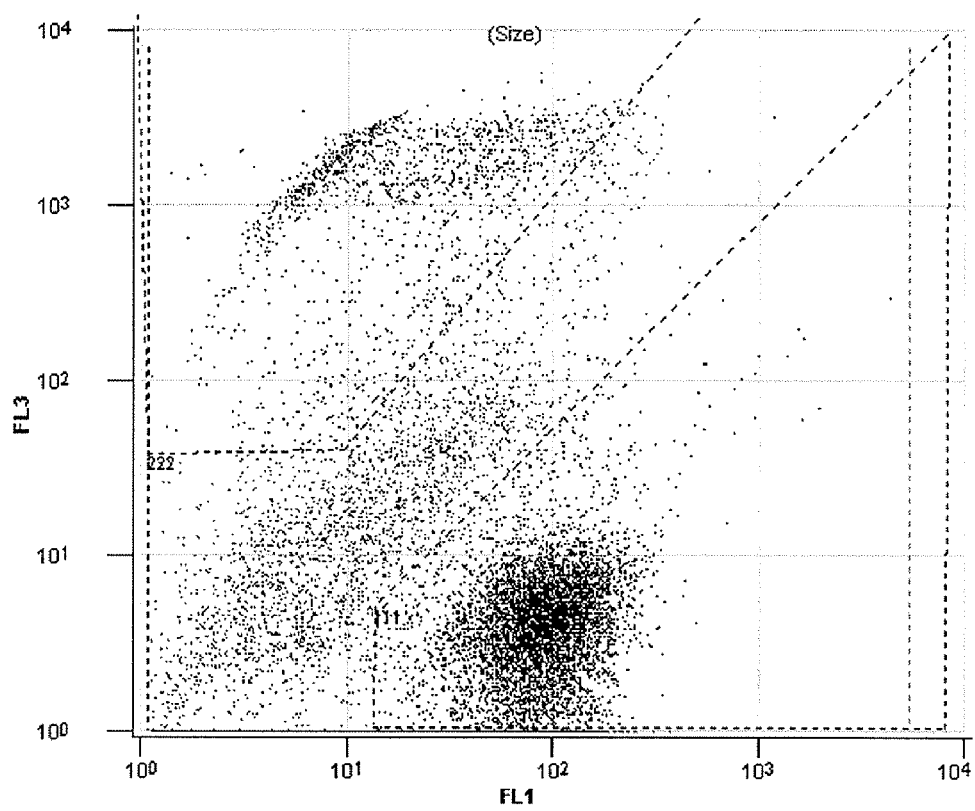
FIG. 7 shows the fluorescence activated cell sorting (FACS) profile for TK 6 cells after neutron exposure for 1 minute in the absence of BN nanotubes.
Figure 7:
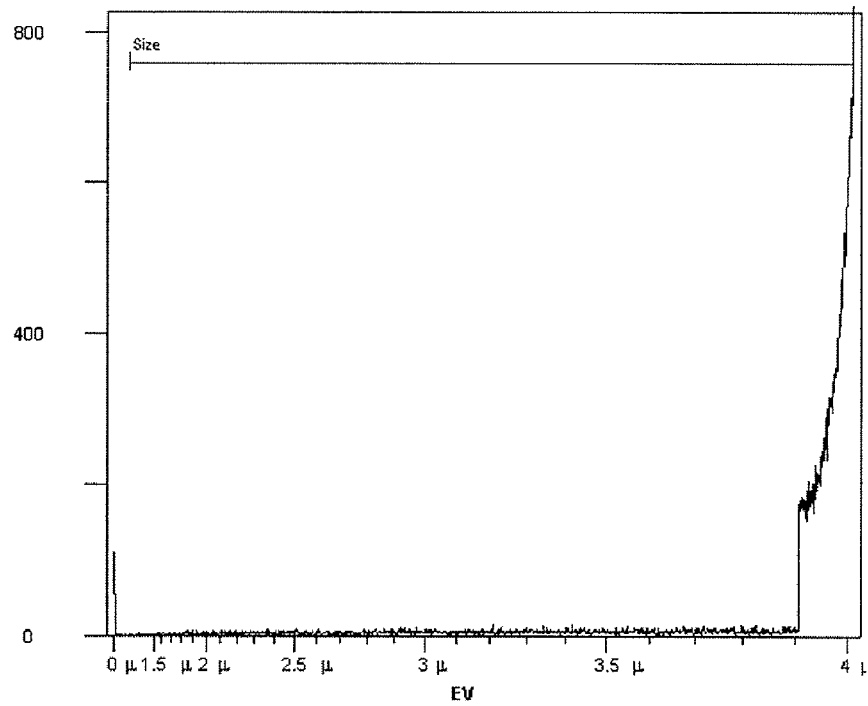

Similar results were obtained when TK6 cells were treated with neutrons alone without the presence of BN nanotubes. More particularly, as shown in FIG. 7 and Table 3 below, there were insubstantial differences in TK6 cell viability and size distribution after such treatment.

TABLE 3

Viability and Size Distribution of TK6 Cells after a 1 Minute Neutron Exposure in the Absence of BN Nanotubes

| Region | FL1 Mean | FL3 Mean | FL1 CV | Pct Gated | Pct Total | Count |
|---|---|---|---|---|---|---|
| Size | 45.0 | 84.6 | 135.84% | 99.59% | 99.59% | 28,737 |
| 111 (live) | 101.0 | 5.92 | 89.19% | 22.16% | 22.07% | 6,368 |
| 222 (dead) | 31.0 | 1,448.2 | 113.34% | 5.06% | 5.04% | 1,455 |

In contrast, significant cell death was observed when cells were exposed to neutron in the presence of BN nanotubes. More particularly, as shown in FIG. 8A and Table 4 below, such treatment left very few intact TK6 cells. Furthermore, as shown in FIG. 8B, not many cell fragments were larger than 2.3 µM diameter.

TABLE 4

Viability and Size Distribution of TK6 Cells after a 1 Minute Neutron Exposure in the Presence of BN Nanotubes

| Region | FL1 Mean | FL3 Mean | FL1 CV | Pct Gated | Pct Total | Count |
|---|---|---|---|---|---|---|
| Size | 2.44 | 2.73 | 54.32% | 94.82% | 94.82% | 120,508 |
| 111 (live) | 44.9 | 10.6 | 111.92% | 0.02% | 0.01% | 19 |
| 222 (dead) | 9.29 | 97.8 | 124.32% | 0.00% | 0.00% | 2 |

Figure 8:
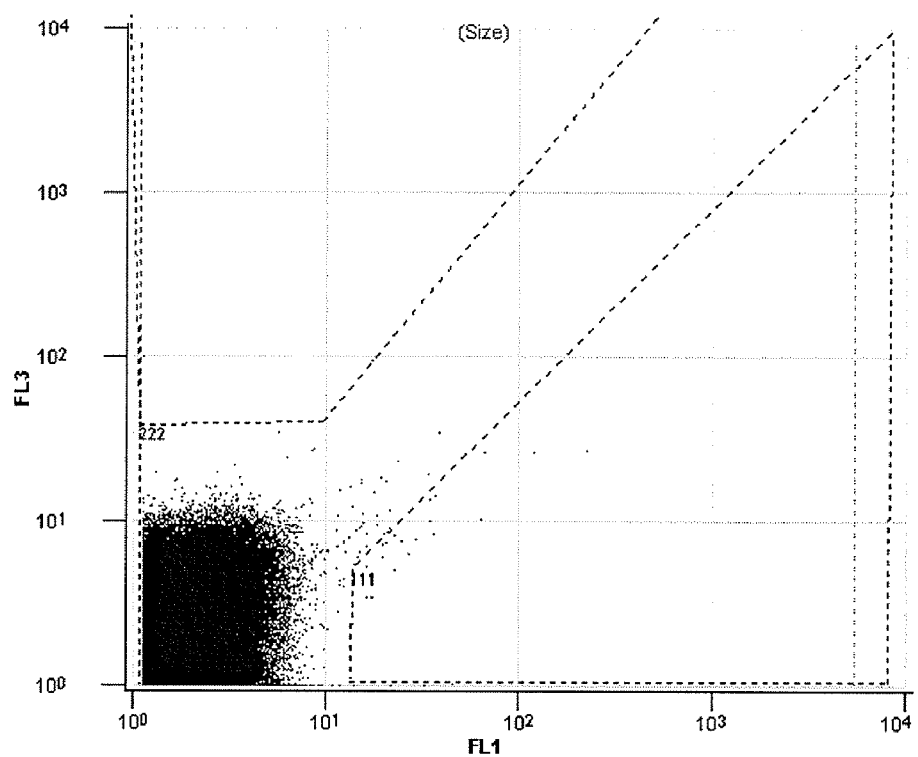
FIG. 8 shows the fluorescence activated cell sorting (FACS) profile for TK 6 cells after neutron exposure for 1 minute in the presence of BN nanotubes.
Figure 8:
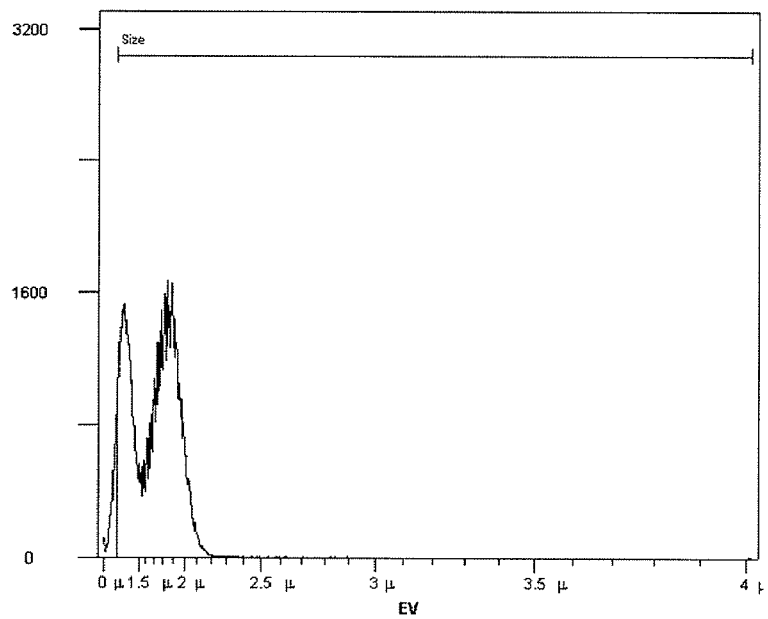

Based on preliminary calculations, it is estimated that there was an excess amount of BN molecules for each TK6 cell in the experiment shown in FIG. 8 and Table 4. More particularly, preliminary calculations indicate that there may have been at least $3.2 \times 10^{12}$ atoms of $^{10}B$ for each TK6 cell in the samples. This estimate is based on the assumption that the molecular weight of BN is 25 g, which corresponds to $6 \times 10^{23}$ molecules of BN, or $3 \times 10^{23}$ atoms of Boron. If one assumes that at least 20% of the Boron atoms in BN are $^{10}B$ isotopes, then there would be approximately $6 \times 10^{22}$ atoms of $^{10}B$ in 25 g of BN. Therefore, 1 mg of BN would contain approximately $2.4 \times 10^{18}$ atoms of $^{10}B$, which, when added to 1.5 ml of TK6 cells with a concentration of approximately $0.5 \times 10^6$ cells per ml (i.e., about $7.5 \times 10^5$ cells), would correspond to at least $3.2 \times 10^{12}$ atoms of $^{10}B$ per cell.

Preliminary calculations also indicate that there was approximately a 1000-fold excess amount of BN nanotubes for each TK6 cell. Such a calculation is based on the assumption that the average diameter for each BN nanotube particle is approximately 1 µM or $1 \times 10^{-14}$ cm. This would correspond to an area of $5.2 \times 10^{-13}$ cm$^3$. Since the density of BN nanotubes is estimated to be approximately 2.27 g/cm$^3$, the mass of each BN nanotube particle would be approximately $1.2 \times 10^{-12}$ g. Therefore, 1 mg of BN nanotubes in each tube would correspond to approximately $8.3 \times 10^8$ BN nanotube particles. Since there were approximately $7.5 \times 10^5$ cells per reaction, this would correspond to about 1,100 BN nanotube per TK6 cell.

Despite the excess amount of BN nanotubes for each TK6 cell, it is envisioned that only a miniscule fraction of the $^{10}B$ atoms within the BN nanotubes were actually activated. More particularly, the activated $^{10}B$ atom to TK6 cell ratio is estimated to be approximately 4:1. This estimate is based on the measurements that the neutron beams were applied to the cells in each vial at $10^7/cm^2$-second for 60 seconds, and the cross-sectional area of each TK6 cell was less than 0.1 cm$^2$. This would amount to approximately 6×10$^7$ neutrons. Therefore, at most, 6×10$^7$ active $^{10}$B atoms were available for the 1.5×10$^7$ cells in each reaction mixture. Nonetheless, the significant effect of a miniscule fraction of the activated $^{10}$B atoms on TK6 cells indicates that an effective in vivo BNCT therapy regime can be designed using tumor cell-targeted BNNTs at a low injected concentration, thus minimizing any potential side effects on normal cells.

Figure 9:
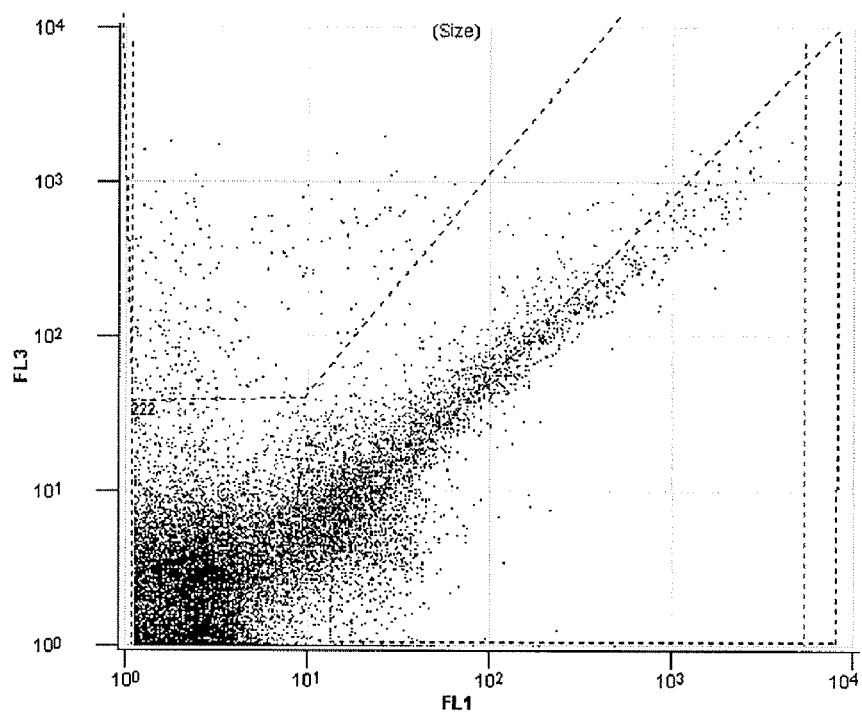
FIG. 9A shows the fluorescence activated cell sorting (FACS) profile for TK6 cells treated with BN nanotubes without any neutron exposure.
FIG. 9B shows the size distribution profile for those cells. The results indicate minor cytotoxic effects.
Figure 9:
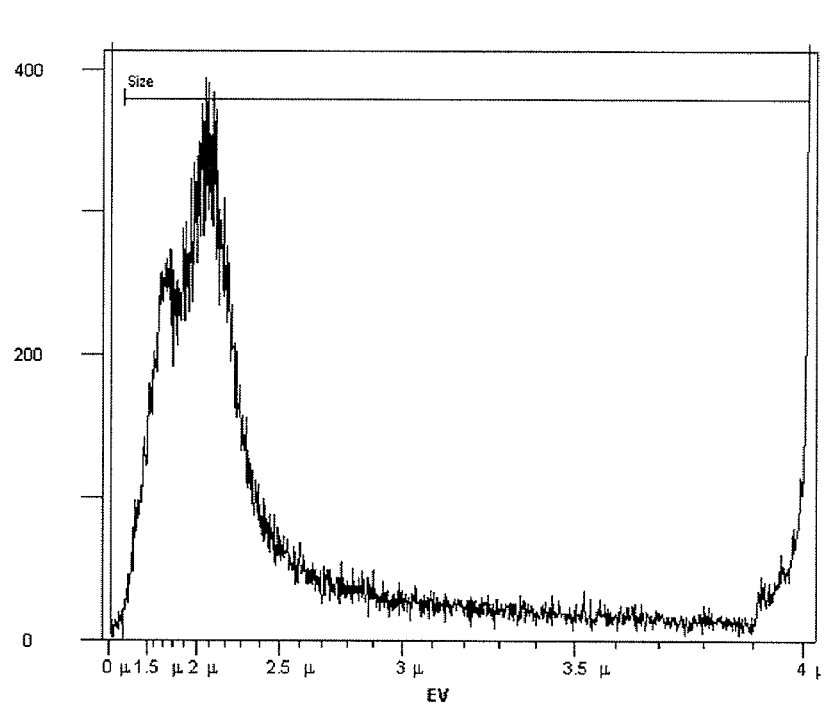

Finally, cytotoxic effects were observed after exposure of TK6 cells to concentrated BN nanotubes in the absence of neutron exposure. However, as shown in FIG. 9 and Table 5 below, such effects were not as significant as when neutron therapy was included (as shown in FIG. 8). Nonetheless, such results indicate that BN nanotubes linked to cell-targeting molecules can be delivered to cancer cells for the purpose of killing them without using any radioisotope, chemical agent, or intentional physical disruption of targeted cells.

TABLE 5

Viability and Size Distribution of TK6 Cells after treatment with BN Nanotubes in the Absence of Neutron Exposure.

| Region | FL1 Mean | FL3 Mean | FL1 CV | Pct Gated | Pct Total | Count |
|---|---|---|---|---|---|---|
| Size | 8.04 | 5.71 | N/A | 95.69% | 95.69% | 66,028 |
| 111 (live) | 181.2 | 77.6 | N/A | 2.22% | 2.13% | 1,467 |
| 222 (dead) | 7.73 | 295.6 | 144.78% | 0.41% | 0.39% | 269 |

Example 6

Interaction of BN Nanotubes with TK6 Tumor Cells

Figure 10:
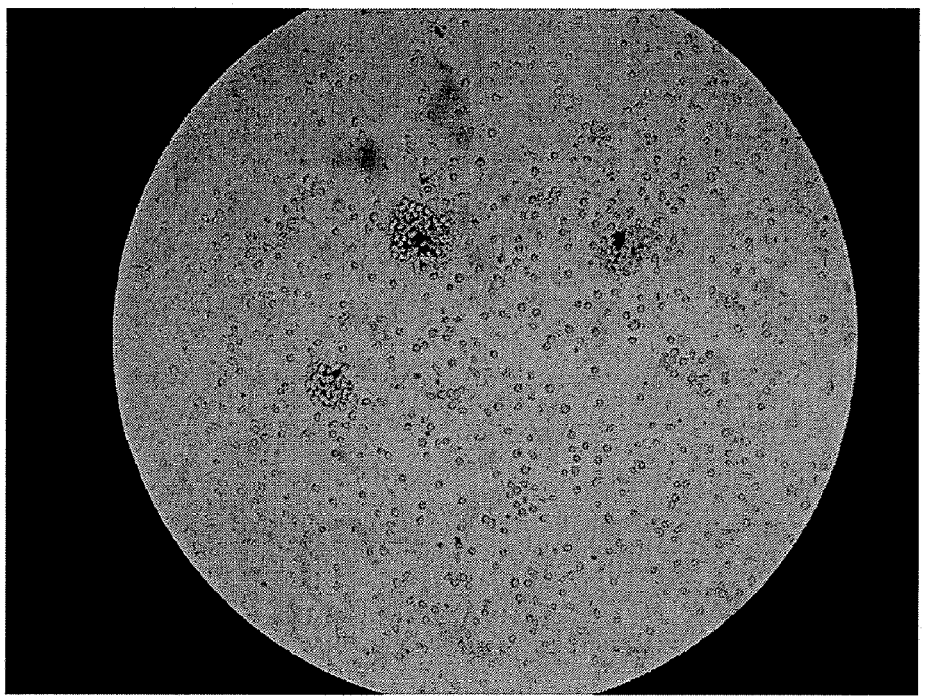
FIG. 10A shows a cell culture of TK6 cells grown in the presence of BN nanotubes without neutron exposure.
FIG. 10B shows a cell culture of TK6 cells grown after neutron exposure for 1 minute in the absence of BN nanotubes.
Figure 10:
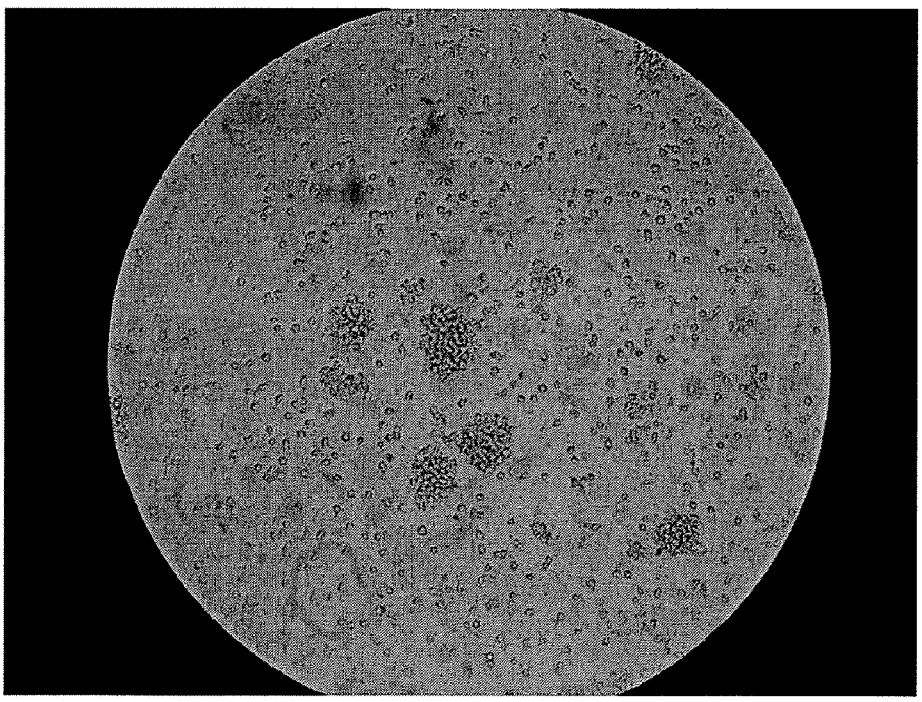

Additional experiments confirm that both BN nanotubes and neutron exposure are required for substantially killing tumor cells in the present invention. For instance, as shown in FIG. 10A, significant cytotoxic effects were not observed on control TK6 cells after they were re-cultured and mixed with small quantities of BN nanotubes. Nonetheless, some of the cells clumped around the BN nanotubes (black dots). Likewise, as shown in FIG. 10B, the same amount of growth was observed after re-cultured cells that were exposed to neutron beams for 1 minute in the absence of BN nanotubes were re-cultured.

Example 7

Encapsulation of BNNT's with Chitosan

A solution containing 200 µg of Zn porphyrin (5, 10, 15, 20-tetraphenyl 21H, 23H Zn porphyrin; 200 µl from a 1 mg/ml solution in 95% ethanol), 100 µg of Chitosan (2 ml from a 0.05 mg/ml solution in 1% acetic acid), and 1.25 mg of the previously prepared BN nanotubes were mixed in a solution to a final acetic acid concentration of about 1%. The solution was then sonicated for 10 minutes using a Cell Disruptor (VirSonic, Gardiner, N.J.) with a ⅛ diameter microprobe at 30% of full power.

After the completion of sonication, about 150 µl of the sonicated solution was electrosprayed onto an aluminum foil sample that was pre-rinsed with ethanol and heat-dried on a hot plate adjusted to approximately 100° C. A Vestec Corporation Electrospray apparatus was used for the above experiment. The electro-spray voltage was set at about 4,250 volts, and the flow rate was adjusted to 1 uL/min. The nozzle of the electrospray contained a 10 µl syringe, which was placed about 2 cm from the foil surface.

Figure 11:
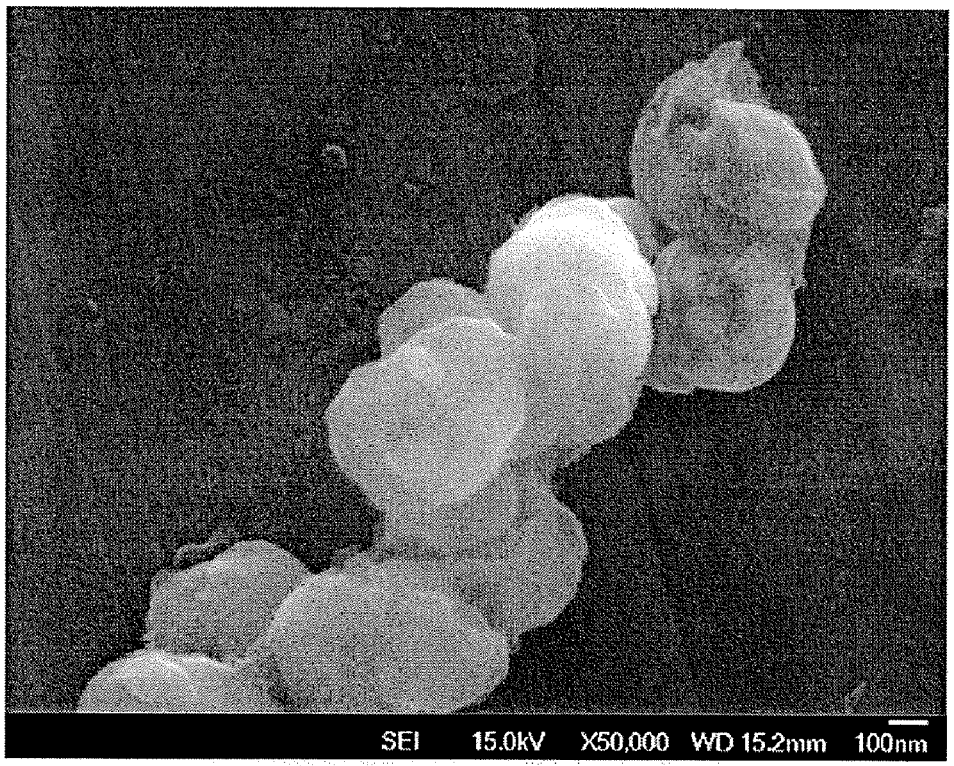
FIG. 11 shows scanning electron micrograph (SEM) images of chitosan-coated BN nanotubes on aluminum foils after electrospray treatment. The BN nanotubes appear to be chitosan-coated, as demonstrated by particle dimensions that exceed 100 nm, as well as by the roughness of the surface when compared to the images of un-coated BNNT's in FIG. 4.
Figure 11:

FIG. 11 shows electro-sprayed BNNTs on the aluminum foil. The BNNT's in FIG. 11A appear to be aggregated, whereas the BNNT in FIG. 11B appears isolated. More importantly, the BNNT's appear to be chitosan-coated, as indicated by particle dimensions that exceed 100 nm, as well as by the roughness of the surface when compared to the images of un-coated BNNT's in FIG. 4.

Once dried, the coated BNNT's appeared as brown spots on the foil. Such discolored regions were cut from the foil and placed in 3 mL of water, which, at neutral pH, did not dissolve the chitosan coating. The BNNT's were then sonicated for 5 minutes in a Cole-Parmer Ultrasonic Cleaner low energy sonic bath (Model B200, 19 W output power) to remove the particles from the foil and form a stable suspension of them. Next, the liquid was taken off and centrifuged for 5 minutes at 4,000 rpm. The recovered particles were deposited as a sediment at the bottom of the centrifuge tube.

Without being bound by theory, one can estimate that about ~20 trillion molecules of BNNTs were electro-sprayed onto the aluminum foil in the above experiment. This is based on the calculation that each BNNT molecule has a volume of 1.57×10$^3$ nm$^3$ (or 1.57×10$^{-18}$ cm$^3$), which is based on the estimate that BNNTs are 10 nm in diameter (5 nm radius) and 20 nm in height. Thus, the formula below would yield the aforementioned volume:

$$V = \pi r^2 h$$

$$V = (3.14)(25)(20) = 1.57 \times 10^3 \text{ nm}^3$$

Conversion of units yields $$V = 1.57 \times 10^{-18} \text{ cm}^3$$

Assuming that each BNNT has a density of about 3 g/cm$^3$, each would weigh about 4.71×10$^{-18}$ g. Thus, the number of BNNTs in 1.25 mg of the 2 ml solution used would be about 2.7×10$^{14}$. Likewise, the number of BNNTs in 1 µL of the solution would be about 1.3×10$^{11}$. Therefore, 150 µL of the electrosprayed solution would contain about 1.95×10$^{13}$ or about ~20 trillion BNNT's.

Example 8

Conjugation of Chitosan-coated BNNT's to Anti-*E. coli* IgG's

Figure 12:
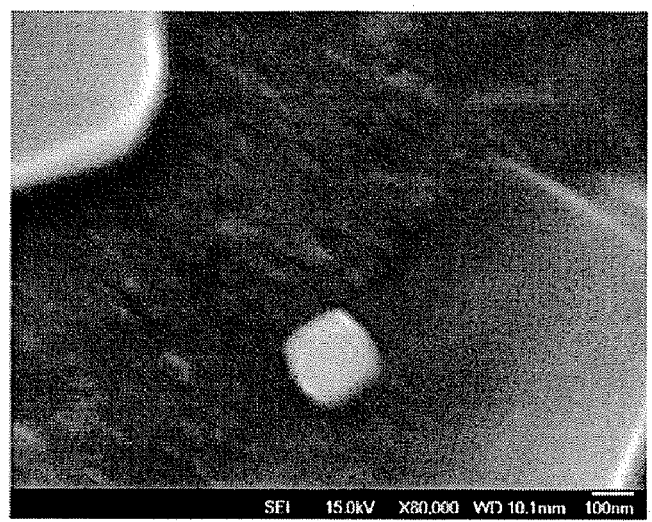
FIG. 12A shows an SEM image of an individual BNNT from a chitosan-coated BNNT solution that was conjugated to anti-*E. coli* IgG's and incubated with *E. coli* cells.
FIGS. 12B and 12C show SEM images of *E. coli* cells after the treatment. As indicated by the arrows, the cells have knob-like structures on their surfaces that appear to be the same size and shape as the chitosan-coated BNNT's in FIG. 12A.
Figure 12:
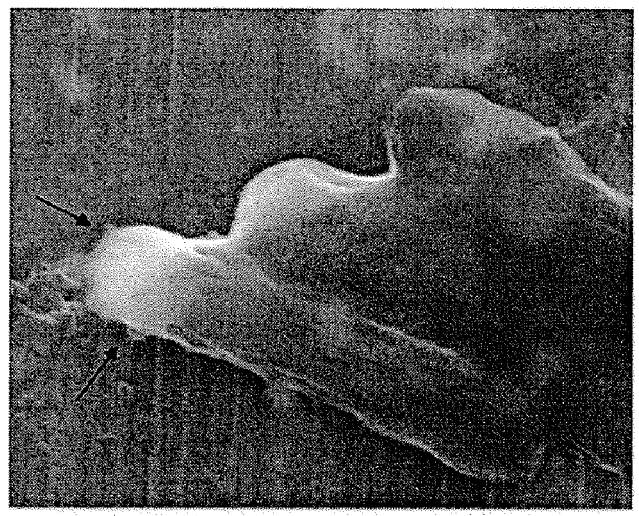
Figure 12:

The encapsulated BNNTs from Example 7 were sampled from the precipitate in 50 µL of the pH 6.5-7 water and maleimided by reacting with Sulfosuccinimidyl-4-(N-maleimidomethyl)cyclohexane-1-carboxylate (Sulfo-SMCC). Next, 50 µl of a mouse monoclonal antibody solution specific for *E. coli* cell surface antigens (AbCam, ab20386 at 0.25 mg/ml) was activated using SATP (N-succinimidyl 3-(acetylthio)propionate). The two solutions were mixed at room temperature for 60 minutes so that the maleimided chitosan-coated BNNTs were chemically bound to the SATP reduced *E. coli* antibodies through attachment to the sulfhydryl (SH) groups on the antibodies. FIG. 12A shows an SEM image of an individual BNNT after the above treatment.

Example 9

Binding of IgG-Conjugated BNNT's to *E. coli* Cells

To demonstrate targeted delivery of BNNT's, the IgG-conjugated BNNT's from Example 8 were mixed with a culture of *E. coli* cells and analyzed by scanning electron microscopy (SEM) using a JEOL 7000F SEM Field Emission Electron Microscope. Briefly, *E. coli* cells were grown to about $1\times10^7$ cells/ml. The cells were then harvested and re-suspended in about 10 ml of PBS (Phosphate Buffered Saline) to a final concentration of $1\times10^6$ cells/ml. Next, about 5 µL of the IgG-conjugated BNNT's from Example 8 was added to the cell suspension. The suspension was mixed at room temperature for about 1 minute. Thereafter, the cells were fixed for SEM analysis.

To prepare the cells for SEM analysis, the cells were first re-suspended in 2.5% glutaraldehyde for 2 hrs. The cells were then washed twice in distilled water with 20 minutes of incubation in the water between the centrifugation and decanting steps. Next, the samples were dehydrated by the gradient ethanol method, where the samples were first washed in 50% ethanol for 15 minutes, then 75% ethanol for 15 minutes, then 95% ethanol for 15 minutes, and then absolute ethanol for 15 minutes. Thereafter, the cells were deposited on 1 cm SEM targets and dried in a dessicator. After dessication, the targets were coated with a 3% (w/v) ammonium molybdate solution and dried again in the dessicator. SEM images of target samples were then obtained by slowly increasing electron beam energy from 1 KV.

Figure 13:
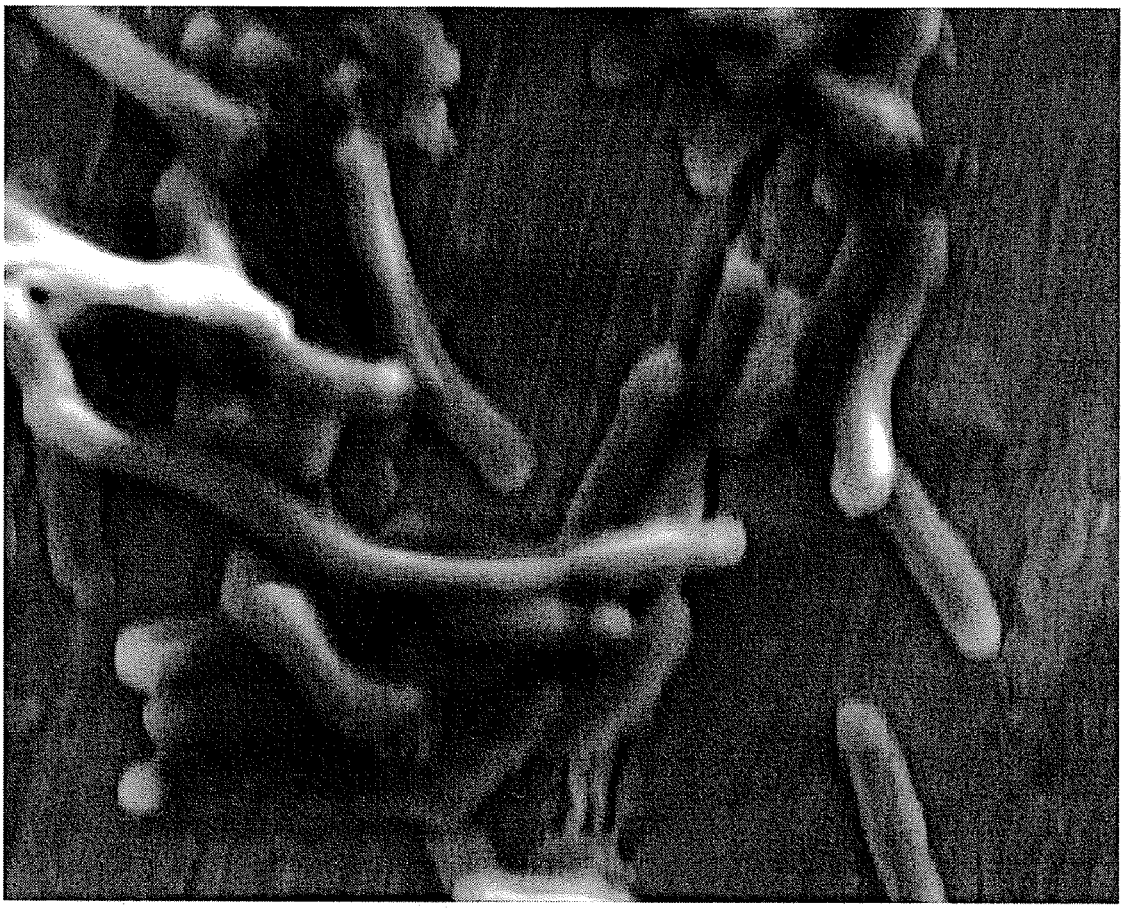
FIG. 13 shows an SEM image of *E. coli* cells after incubation with chitosan-coated BNNT's that were not conjugated to any antibodies. The cells appear smooth without any bound BNNT's on their surfaces.

FIG. 12A shows an SEM image of an individual chitosan-coated BNNT after the above treatment. FIGS. 12B and 12C show SEM images of *E. coli* cells after the treatment. As indicated by the arrows, the cells have knob-like structures on their surfaces that appear to be the same size and shape as the chitosan-coated BNNT's in FIG. 12A. In contrast, FIG. 13 shows an SEM image of *E. coli* cells after incubation with chitosan coated BNNT's (from Example 7) that were not conjugated to any antibodies. There's no indication that the bacterial cells in this control experiment contained any bound BNNT on their cell wall surfaces.

A parallel SEM analysis approach was carried out with another batch of *E. coli* cells. In particular, after incubation with the IgG-conjugated BNNT's, the bacterial cells were re-suspended in pure methanol rather than glutaraldehyde. In addition, after the washing and dehydration steps, the cells were dried by vacuum evaporation rather than dessication. In addition, the coating step with ammonium molybdate was omitted. The SEM image for the above experiment in FIG. 14A shows that the bacterial cells have a white, sponge-like coating.

Figure 14:
FIG. 14A shows another SEM image of *E. coli* cells after incubation with chitosan-coated BNNT's that were conjugated with anti-*E. coli* IgG's.
FIG. 14B shows an energy dispersive x-ray spectrum (EDS) of the sample in FIG. 14A.
Figure 14:
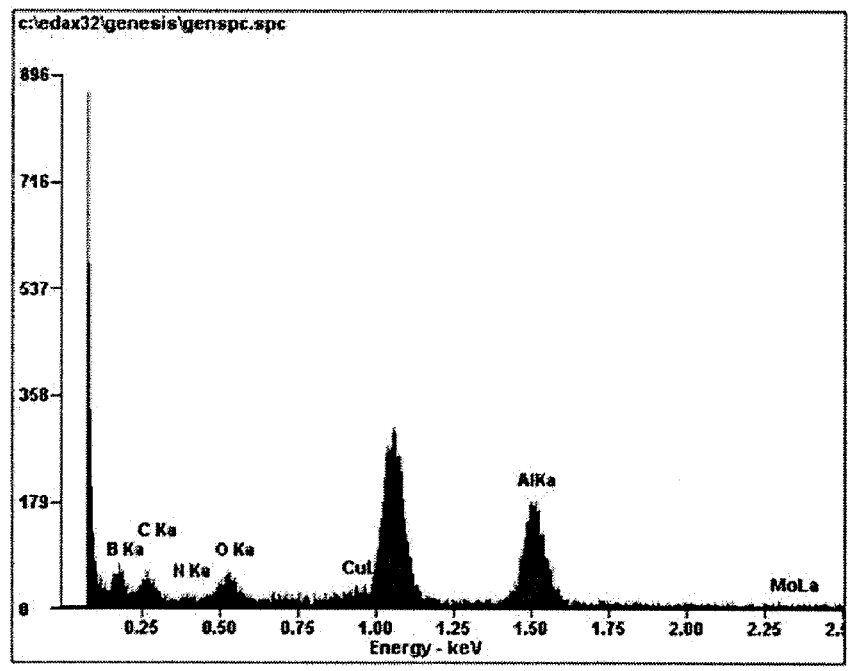

FIG. 14B shows an energy dispersive x-ray spectrum (EDS) of the sample in FIG. 14A. The spectrum in FIG. 14B was generated by energy dispersive x-ray spectroscopy (EDS) which is part of the JEOL 7000F SEM Field Emission Electron Microscope. EDS is a chemical microanalysis technique performed in conjunction with a scanning electron microscope (SEM). The technique utilizes x-rays that are emitted from the sample during bombardment by the electron beam to characterize the elemental composition of the analyzed volume. The spectrum shows a higher boron peak than a carbon peak. However, boron peaks are usually absent in bacterial cells.

Taken together, the preliminary results in Examples 8 and 9 indicate that individual BNNTs can be conjugated to cell-targeting antibodies and attached to the targeted cells. One can use the same approach (or similar approaches) for the targeted delivery of BNNT's to specific types of cancer cells within the human body. As mentioned previously, such targeted delivery has been demonstrated in the past using other nano-particles.

The novel therapies described herein are generally applicable to all types of cancers. They potentially have the ability, through one treatment, or a series of treatments, to completely cure a person of a particular cancer. Some embodiments of the invention, such as those comprising the radiation-laden nanostructure-IgG species and the diffuse activation of BNnt-IgG species, are even capable of seeking out metastasized cancer cells and destroying them. Embodiments comprising BN nanotube-IgG species provide an excellent means for implementing boron neutron capture therapy—which is currently gaining favor around the globe. BNNT-based therapies have the potential to make BNCT significantly more powerful and specific than it currently is, and allow it to treat much larger tumor masses and organs. In addition, techniques using ultrasound waves to target carbon nanotubes delivered by IgGs specifically to tumor sites, can kill a tumor without the use of nuclear radiation. This latter group of techniques not only provides an alternative way to target and injure or kill cells (fragmenting tubes), but also shows how to empty a tube without having to develop and validate a specific enzyme-activated removable cap. Finally, the present invention provides a way to systematically characterize the specificity of the IgG "tractor" for each patient before beginning the treatment phase through the use of a small amount of radioisotopes attached to an IgG via the mechanisms mentioned. The small amount of radiation delivered by such a tractor can act as a tracer in the body, capable of being viewed using a radioactive scanning technique such as PET.

Lastly, any of the methods described herein may be applicable for treating other maladies and should not be construed as being limited to cancer therapies and/or diagnostic techniques. As an example, BNCT has been shown to be applicable for palliative treatment of rheumatoid arthritis (its use being termed radiation synovectomy). See Yanch et al., Med. Phys., (1999) 26: 364-375, incorporated herein by reference.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method comprising:
    a) attaching an antibody (IgG) cell-targeting species to BN nanostructures to form BN nanostructure-cell-targeting composite species;
    b) administering said BN nanostructure-cell-targeting composite species to a mammalian subject such that the BN nanostructure-cell-targeting composite species targets tumors within said subject; and
    c) activating at least some of the boron atoms in the BN nanostructure-cell-targeting composite species;
        wherein the activating step comprises irradiating the subject with transdermal neutrons to activate the boron atoms.

2. The method of claim 1, wherein the BN nanostructure-cell-targeting composite species is a BN nanotube-IgG composite species.

3. The method of claim 2, wherein BN nanotubes are attached to IgG molecules via a covalent linker.

4. The method of claim 1, wherein the BN nanostructures are encapsulated with a bio-polymer material.

5. The method of claim 4, wherein the bio-polymer material is chitosan.

6. The method of claim 4, wherein the antibody (IgG) cell-targeting species is attached to the BN nanostructures through the bio-polymer.

7. The method of claim 2, wherein the BN nanotube-IgG composite species further targets metastasized cells.

8. The method of claim 1, wherein the activating step comprises irradiating the subject with a diffuse pattern of neutrons.

* * * * *

UNITED STATES PATENT AND TRADEMARK OFFICE
CERTIFICATE OF CORRECTION

PATENT NO. : 7,824,660 B2  Page 1 of 1
APPLICATION NO. : 12/112986
DATED : November 2, 2010
INVENTOR(S) : Dan A. Buzatu et al.

It is certified that error appears in the above-identified patent and that said Letters Patent is hereby corrected as shown below:

Title Page, Item [75]
 Please correct inventor name from:

Delete "Alex Birls"

should read

Alex Biris

Signed and Sealed this

Thirteenth Day of September, 2011

David J. Kappos
*Director of the United States Patent and Trademark Office*